United States Patent [19]
Quax et al.

[11] Patent Number: 5,364,782
[45] Date of Patent: Nov. 15, 1994

[54] MUTANT MICROBIAL α-AMYLASES WITH INCREASED THERMAL, ACID AND/OR ALKALINE STABILITY

[75] Inventors: Wilhelmus J. Quax, Voorschoten, Netherlands; Yves Laroche, Brussels, Belgium; Adrianus W. H. Vollebregt, Naaldwijk, Netherlands; Patrick Stanssens, St. Denijs Westrem, Belgium

[73] Assignees: Gist-Brocades N.V., Delft, Netherlands; Plant Genetic Systems N.V., Brussels,

[21] Appl. No.: 623,953
[22] PCT Filed: Jun. 27, 1990
[86] PCT No.: PCT/EP90/01042
 § 371 Date: Dec. 2, 1990
 § 102(e) Date: Dec. 2, 1990
[87] PCT Pub. No.: WO91/00353
 PCT Pub. Date: Jan. 10, 1991

[30] Foreign Application Priority Data

Jun. 29, 1989 [EP] European Pat. Off. ............ 89201735

[51] Int. Cl.$^5$ .................. C12N 9/28; C12N 15/56; C12N 1/21; D06M 16/00
[52] U.S. Cl. .................. 435/202; 435/252.3; 435/263; 435/275; 435/320.1; 536/23.2
[58] Field of Search .......... 435/202, 69.1, 320.1, 435/252.3, 263, 275; 536/23.2

[56] References Cited

U.S. PATENT DOCUMENTS

| | | | |
|---|---|---|---|
| 4,394,443 | 7/1983 | Weissman et al. | 435/6 |
| 4,740,461 | 4/1988 | Kaufman | 435/69.1 |

FOREIGN PATENT DOCUMENTS

| | | |
|---|---|---|
| 0057976 | 8/1982 | European Pat. Off. |
| 0134048 | 3/1985 | European Pat. Off. |
| 0189838 | 8/1986 | European Pat. Off. |
| 0224294 | 6/1987 | European Pat. Off. |
| 0252666 | 1/1988 | European Pat. Off. |
| 0253455 | 1/1988 | European Pat. Off. |
| 0285123 | 10/1988 | European Pat. Off. |

OTHER PUBLICATIONS

Gray et al., Structural Genes Encoding the Thermophilic alpha-Amylases of *Bacillus stearothermophilus* and *Bacillus licheniformis*, *J. Bacteriol.* (1986) 166:635-643.

Kuhn et al., "N-Terminal Amino Acid Sequence of *Bacillus licheniformis* alpha-Amylase . . . " *J. Bacteriol.* (1982) 149:372-373.

Janin and Wodak, "Structural Domains in Proteins and their Role in the Dynamics of Protein Function", *Prog. Biophys Molec. Biol.* (1983) 42:21-78.

Tomazic and Klibanov, "Why is One *Bacillus* alpha-Amylase More Resistant Against Irreversible Thermoinactivation Than Another?", *J. Biol. Chem.* (1988) 263:3092-3096.

Wigley et al., "The Greater Strength of Arginine:Carboxylate Over Lysine Carboxylate Ion Pairs Implications for the Design of Novel Enzymes and Drugs", *Biochem. and Biophys. Res. Comm.* (1987) 149:927-929.

Morinaga et al., "Improvement of Oligonucleotide-Directed Site-Specific Mutagenesis using Double-Stranded Plasmid DNA", *Bio/Technology* (1984) 2:636-639.

Folk and Hofstetter, "A Detailed Mutational Analysis of the Eucaryotic tRNA 1 met Gene Promoter", *Cell* (1983) 33:585-593.

Lehtovaara et al., "A New Method for Random Mutagenesis of Complete Genes:1 Enzymatic Generation of Mutant Libraries *in vitro*", *Prot. Eng.* (1988) 2:63-68.

(List continued on next page.)

*Primary Examiner*—Keith C. Furman
*Attorney, Agent, or Firm*—Barbara Rae-Venter

[57] ABSTRACT

Thermostable and acid stable α-amylases are provided as expression products of genetically engineered α-amylase genes isolated from microorganisms, preferably belonging to the class of Bacilli. Both chemical and enzymatic mutagenesis methods are e.g. the bisulphite method and enzymatic misincorporation on gapped heteroduplex DNA. The mutant α-amylases have superior properties, e.g. improved thermostability over a broad pH range, for industrial application in starch processing and textile desizing.

6 Claims, 24 Drawing Sheets

OTHER PUBLICATIONS

Yuuki et al., "Complete Nucleotide Sequence of a Gene Coding for Heat-and pH Stable alpha-amylase of *Bacillus licheniformis* . . . ", *J. Biochem.* (1985) 98:1147–1156.

Nakajima et al., "Comparison of Amino Acid Sequences of Eleven Different alpha-amylases", *Appl. Microbiol. Biotechnol.* (1986) 23:355–360.

Shortle and Botstein, "Directed Mutagenesis with Sodium Bisulfite", *Methods Enzymol* (1983) 100:457–468.

Smith., "In Vitro Mutagenesis", *Ann. Rev. Genet.* (1985) 19:423–462.

Coker and Venkatasubramanian, "High Fructose Corn Syrup", *Biotechnology* (1985) 165–171.

Kramer et al., "The Gapped Duplex DNA Approach to Oligonucleotide-directed Mutation Construction:", *Nucl. Acids Res.* (1984) 12:9441–9457.

Stanssens et al., "Efficient Oligonucleotide-directed Construction of Mutations in Expression Vectors by the Gapped Duple DNA Method using Alternating Selectable Markers", *Nucl. Acids Res.* (1989) 17:4441–4455.

Fowler et al., "Characterization of Mutational Specificity Within the *lacI* Gene for a *mutD*5 Mutator Strain of *Escherichia coli* . . . " *J. Bacteriol.* (1986) 167:130–137.

Shortle et al., "Gap Misrepair Mutagenesis:Efficient Site-directed Induction of Transition, Transversion, and Frameshift Mutations *In vitro*", *Proc. Natl. Acad. Sci. USA* (1982) 79:1588–1592.

Zell and Fritz, "DNA Mismatch-repair in *Escherichia coli* Counteracting the Hydrolytic Deamination of 5-methyl-cytosine Residues", *EMBO. J.* (1987) 6:1809–1815.

Gryczan et al., "Characterization of Staphylococcus aureus Plasmids Introduced by Transformation into *Bacillus subtilis*", *J. Bacteriol.* (1978) 134:318–329.

Sanger et al., "DNA Sequencing with Chain-terminating Inhibitors", *Proc. Natl. Acad. Sci. USA* (1977) 74:5463–5467.

De Boer et al., "The *tac* Promoter:A Functional Hybrid Derived from the *trp* and *lac* Promoters", *Proc. Nal. Acad. Sci. USA* (1983) 80:21–25.

Yutani et al. 1985, Adv. Biophys. 20: 13–29.

Yuecki et al. 1985, J. Biochem. 98: 1147–1156.

Ogasahara et al. 1970, J. Biochemisty 67(1): 65–75.

Jaenicko, R. 1991, Eur. J. Biochem. 202: 715–728.

```
          10        20        30        40        50        60
AATTCACCTCGAAAGCAAGCTGATAAACCGATACAATTAAAGGCTCCTTTTGGAGCCTTT 70        80        90       100       110       120
TTTTTTGGAGATTTTCAACGTGAAAAAATTATTATTCGCAATTCCAAGCTAATTCACCTC 130       140       150       160       170       180
GAAAGCAAGCTGATAAACCGATACAATTAAAGGCTCCTTTTGGAGCCTTTTTTTTTGGAG 190       200       210       220       230       240
ATTTTCAACGTGAAAAAATTATTATTCGCAATTCCAAGCTCTGCCTCGCGCGTTTCGGTG 250       260       270       280       290       300
ATGACGGTGAAAACCTCTGACACATGCAGCTCCCGGAGACGGTCACAGCTTGTCTGTAAG 310       320       330       340       350       360
CGGATGCAGATCACGCGCCCTGTAGCGGCGCATTAAGCGCGGCGGGTGTGGTGGTTACGC 370       380       390       400       410       420
GCAGCGTGACCGCTACACTTGCCAGCGCCCTAGCGCCCGCTCCTTTCGCTTTCTTCCCTT 430       440       450       460       470       480
CCTTTCTCGCCACGTTCGCCGGCTTTCCCCGTCAAGCTCTAAATCGGGGGCTCCCTTTAG 490       500       510       520       530       540
GGTTCCGATTTAGTGCTTTACGGCACCTCGACCCCAAAAAAACTTGATTAGGGTGATGGTT 550       560       570       580       590       600
CACGTAGTGGGCCATCGCCCTGATAGACGGTTTTTCGCCCTTTGACGTTGGAGTCCACGT 610       620       630       640       650       660
TCTTTAATAGTGGACTCTTGTTCCAAACTGGAACAACACTCAACCCTATCTCGGTCTATT 670       680       690       700       710       720
CTTTTGATTTATAAGGGATTTTGCCGATTTCGGCCTATTGGTTAAAAAATGAGCTGATTT 730       740       750       760       770       780
AACAAAAATTTAACGCGAATTTTAACAAAATATTAACGTTTACAATTTGATCTGCGCTCG 790       800       810       820       830       840
GTCGTTCGGCTGCGGCGAGCGGTATCAGCTCACTCAAAGGCGGTAATACGGTTATCCACA 850       860       870       880       890       900
GAATCAGGGGATAACGCAGGAAAGAACATGTGAGCAAAAGGCCAGCAAAAGGCCAGGAAC 910       920       930       940       950       960
CGTAAAAAGGCCGCGTTGCTGGCGTTTTTCCATAGGCTCCGCCCCCCTGACGAGCATCAC 970       980       990      1000      1010      1020
AAAAATCGACGCTCAAGTCAGAGGTGGCGAAACCCGACAGGACTATAAAGATACCAGGCG 1030      1040      1050      1060      1070      1080
TTTCCCCCTGGAAGCTCCCTCGTGCGCTCTCCTGTTCCGACCCTGCCGCTTACCGGATAC 1090      1100      1110      1120      1130      1140
CTGTCCGCCTTTCTCCCTTCGGGAAGCGTGGCGCTTTCTCAATGCTCACGCTGTAGGTAT
```

FIG. IA

```
      1150      1160      1170      1180      1190      1200
CTCAGTTCGGTGTAGGTCGTTCGCTCCAAGCTGGGCTGTGTGCACGAACCCCCCGTTCAG 1210      1220      1230      1240      1250      1260
CCCGACCGCTGCGCCTTATCCGGTAACTATCGTCTTGAGTCCAACCCGGTAAGACACGAC 1270      1280      1290      1300      1310      1320
TTATCGCCACTGGCAGCAGCCACTGGTAACAGGATTAGCAGAGCGAGGTATGTAGGCGGT 1330      1340      1350      1360      1370      1380
GCTACAGAGTTCTTGAAGTGGTGGCCTAACTACGGCTACACTAGAAGGACAGTATTTGGT 1390      1400      1410      1420      1430      1440
ATCTGCGCTCTGCTGAAGCCAGTTACCTTCGGAAAAAGAGTTGGTAGCTCTTGATCCGGC 1450      1460      1470      1480      1490      1500
AAACAAACCACCGCTGGTAGCGGTGGTTTTTTTGTTTGCAAGCAGCAGATTACGCGCAGA 1510      1520      1530      1540      1550      1560
AAAAAAGGATCTCAAGAAGATCCTTTGATCTTTTCTACGGGGTCTGACGCTCAGTGGAAC 1570      1580      1590      1600      1610      1620
GAAAACTCACGTTAAGGGATTTTGGTCATGAGATTATCAAAAAGGATCTTCACCTAGATC 1630      1640      1650      1660      1670      1680
CTTTTAAATTAAAAATGAAGTTTTAAATCAATCTAAAGTATATATGAGTAAACTTGGTCT 1690      1700      1710      1720      1730      1740
GACAGTTACCAATGCTTAATCAGTGAGGCACCTATCTCAGCGATCTGTCTATTTCGTTCA 1750      1760      1770      1780      1790      1800
TCCATAGTTGCCTGACTCCCCGTCGTGTAGATAACTACGATACGGGAGGGCTTACCATCT 1810      1820      1830      1840      1850      1860
GGCCCCAGTGCTGCAATGATACCGCGAGACCCACGCTCACCGGCTCCAGATTTATCAGCA 1870      1880      1890      1900      1910      1920
ATAAACCAGCCAGCCGGAAGGGCCGAGCGCAGAAGTGGTCCTGCAACTTTATCCGCCTCC 1930      1940      1950      1960      1970      1980
ATCCAGTCTATTAATTGTTGCCGGGAAGCTAGAGTAAGTAGTTCGCCAGTTAATAGTTTG 1990      2000      2010      2020      2030      2040
CGCAACGTTGTTGCCATTGCTGCAGGCATCGTGGTGTCACGCTCGTCGTTTGGTATGGCT 2050      2060      2070      2080      2090      2100
TCATTCAGCTCCGGTTCCCAACGATCAAGGCGAGTTACATGATCCCCCATGTTGTGCAAA 2110      2120      2130      2140      2150      2160
AAAGCGGTTAGCTCCTTCGGTCCTCCGATCGTTGTCAGAAGTAAGTTGGCCGCAGTGTTA 2170      2180      2190      2200      2210      2220
TCACTCATGGTTATGGCAGCACTGCATAATTCTCTTACTGTCATGCCATCCGTAAGATGC 2230      2240      2250      2260      2270      2280
```

FIG. I B

```
TTTTCTGTGACTGGTGAGTACTCAACCAAGTCATTCTGAGAATAGTGTATGCGGCGACCG 2290      2300      2310      2320      2330      2340
AGTTGCTCTTGCCCGGCGTCAACACGGGATAATACCGCGCCACATAGCAGAACTTTAAAA 2350      2360      2370      2380      2390      2400
GTGCTCATCATTGGAAAACGTTCTTCGGGGCGAAAACTCTCAAGGATCTTACCGCTGTTG 2410      2420      2430      2440      2450      2460
AGATCCAGTTCGATGTAACCCACTCGTGCACCCAACTGATCTTCAGCATCTTTTACTTTC 2470      2480      2490      2500      2510      2520
ACCAGCGTTTCTGGGTGAGCAAAAACAGGAAGGCAAAATGCCGCAAAAAAGGGAATAAGG 2530      2540      2550      2560      2570      2580
GCGACACGGAAATGTTGAATACTCATACTCTTCCTTTTTCAATATTATTGAAGCAGACAG 2590      2600      2610      2620      2630      2640
TTTTATTGTTCATGATGATATATTTTTATCTTGTGCAATGTAACATCAGAGATTTTGAGA 2650      2660      2670      2680      2690      2700
CACAACGTGGCTTTGTTGAATAAATCGAACTTTTGCTGAGTTGACTCCCCGCGCGCGATG 2710      2720      2730      2740      2750      2760
GGTCGAATTTGCTTTCGAAAAAAAAGCCCGCTCATTAGGCGGGCTAAAAAAAAGCCCGCT 2770      2780      2790      2800      2810      2820
CATTAGGCGGGCTCGAATTTCTGCCATTCATCCGCTTATTATCACTTATTCAGGCGTAGC 2830      2840      2850      2860      2870      2880
AACCAGGCGTTTAAGGGCACCAATAACTGCCTTAAAAAAATTACGCCCCGCCCTGCCACT 2890      2900      2910      2920      2930      2940
CATCGCAGTACTGTTGTAATTCATTAAGCATTCTGCCGACATGGAAGCCATCACAGACGG 2950      2960      2970      2980      2990      3000
CATGATGAACCTGAATCGCCAGCGGCATCAGCACCTTGTCGCCTTGCGTATAATATTTGC 3010      3020      3030      3040      3050      3060
CCATAGTGAAAACGGGGGCGAAGAAGTTGTCCATATTCGCCACGTTTAAATCAAAACTGG 3070      3080      3090      3100      3110      3120
TGAAACTCACCCAGGGATTGGCTGAGACGAAAAACATATTCTCAATAAACCCTTTAGGGA 3130      3140      3150      3160      3170      3180
AATAGGCCAGGTTTTCACCGTAACACGCCACATCTTGCGAATATATGTGTAGAAACTGCC 3190      3200      3210      3220      3230      3240
GGAAATCGTCGTGGTATTCACTCCAGAGCGATGAAAACGTTTCAGTTTGCTCATGGAAAA 3250      3260      3270      3280      3290      3300
CGGTGTAACAAGGGTGAACACTATCCCATATCACCAGCTCACCGTCTTTCATTGCCATAC 3310      3320      3330      3340      3350      3360
GAAATTCCGGATGAGCATTCATCAGGCGGGCAAGAATGTGAATAAAGGCCGGATAAAACT
```

FIG. I C

```
      3370      3380      3390      3400      3410      3420
TGTGCTTATTTTTCTTTACGGTCTTTAAAAAGGCCGTAATATCCAGCTAAACGGTCTGGT 3430      3440      3450      3460      3470      3480
TATAGGTACATTGAGCAACTGACTGAAATGCCTCAAAATGTTCTTTACGATGCCATTGGG 3490      3500      3510      3520      3530      3540
ATATATCAACGGTGGTATATCCAGTGATTTTTTTCTCCATTTTAGCTTCCTTAGCTCCTG 3550      3560      3570      3580      3590      3600
AAAATCTCGATAACTCAAAAAATACGCCCGGTAGTGATCTTATTTCATTATGGTGAAAGT 3610      3620      3630      3640      3650      3660
TGGAACCTCTTACGTGCCGATCAACGTCTCATTTTCGCCAAAAGTTGGCCCAGGGCTTCC 3670      3680      3690      3700      3710      3720
CGGTATCAACAGGGACACCAGGATTTATTTATTCTGCGAAGTGATCTTCCGTCACAGGTA 3730      3740      3750      3760      3770      3780
TTTATTCGAAGACGAAAGGGCATCGCGCGCGGGGAATTCCCGGGGATCCGTCGACCTGCA 3790      3800
GCCAAGCTTGGTCTAGAGGTCGA
```

FIG. 1D

```
       10        20        30        40        50        60
GTCTACAAACCCCTTAAAAACGTTTTTAAAGGCTTTTAAGCCGTCTGTACGTTCCTTAAG 70        80        90       100       110       120
GAATTCACACTGGCCTTGGTTAAGGTTAAGATGTGGACGGAATGGGTAAAGTGTAGTAAA 130       140       150       160       170       180
GTACAATTAATCGGGAGCTTAGATGTCCCTTCAACATCTTATATAGAAGGGAAGGTTGGC 190       200       210       220       230       240
AAATGGAAATTGAAAGAATTAACGAGCATACAGTAAAATTTTATATGTCTTACGGAGATA 250       260       270       280       290       300
TTGAAGATCGCGGTTTTGACAGAGAAGAAATTTGGTATAACCGTGAGCGCAGTGAAGAAC 310       320       330       340       350       360
TTTTCTGGGAAGTCATGGATGAAGTTCATGAAGAAGAGGAATTCGAGCTCGCCCGGGGAT 370       380       390       400       410       420
CCAAGGAGGTGATCTAGAGTCATGAAACAACAAAAACGGCTTTACGCCCGATTGCTGACG
                       M   K   Q   Q   K   R   L   Y   A   R   L   L   T 430       440       450       460       470       480
CTGTTATTTGCGCTCATCTTCTTGCTGCCTCATTCTGCAGCAGCGGCGGCAAATCTTAAT
 L   L   F   A   L   I   F   L   L   P   H   S   A   A   A   A   A   N   L   N
                                                             +1
      490       500       510       520       530       540
GGGACGCTGATGCAGTATTTTGAATGGTACATGCCCAATGACGGCCAACATTGGAAGCGT
 G   T   L   M   Q   Y   F   E   W   Y   M   P   N   D   G   Q   H   W   K   R
 5
      550       560       570       580       590       600
TTGCAAAACGACTCGGCATATTTGGCTGAACACGGTATTACTGCCGTCTGGATTCCCCCG
 L   Q   N   D   S   A   Y   L   A   E   H   G   I   T   A   V   W   I   P   P
25
      610       620       630       640       650       660
GCATATAAGGGAACGAGCCAAGCGGATGTGGGCTACGGTGCTTACGACCTTTATGATTTA
 A   Y   K   G   T   S   Q   A   D   V   G   Y   G   A   Y   D   L   Y   D   L
45
      670       680       690       700       710       720
GGGGAGTTTCATCAAAAAGGGACGGTTCGGACAAAGTACGGCACAAAAGGAGAGCTGCAA
 G   E   F   H   Q   K   G   T   V   R   T   K   Y   G   T   K   G   E   L   Q
65
      730       740       750       760       770       780
TCTGCGATCAAAAGTCTTCATTCCCGCGACATTAACGTTTACGGGGATGTGGTCATCAAC
 S   A   I   K   S   L   H   S   R   D   I   N   V   Y   G   D   V   V   I   N
85
      790       800       810       820       830       840
CACAAAGGCGGCGCTGATGCGACCGAAGATGTAACCGCGGTTGAAGTCGATCCCGCTGAC
 H   K   G   G   A   D   A   T   E   D   V   T   A   V   E   V   D   P   A   D
105
      850       860       870       880       890       900
CGCAACCGCGTAATTTCAGGAGAACACCTAATTAAAGCCTGGACACATTTTCATTTTCCG
 R   N   R   V   I   S   G   E   H   L   I   K   A   W   T   H   F   H   F   P
125
      910       920       930       940       950       960
GGGCGCGGCAGCACATACAGCGATTTTAAATGGCATTGGTACCATTTTGACGGAACCGAT
 G   R   G   S   T   Y   S   D   F   K   W   H   W   Y   H   F   D   G   T   D
145
```

FIG.2A

```
        970       980       990      1000      1010      1020
TGGGACGAGTCCCGAAAGCTGAACCGCATCTATAAGTTTCAAGGAAAGGCTTGGGATTGG
 W  D  E  S  R  K  L  N  R  I  Y  K  F  Q  G  K  A  W  D  W
165
       1030      1040      1050      1060      1070      1080
GAAGTTTCCAATGAAAACGGCAACTATGATTATTTGATGTATGCCGACATCGATTATGAC
 E  V  S  N  E  N  G  N  Y  D  Y  L  M  Y  A  D  I  D  Y  D
185
       1090      1100      1110      1120      1130      1140
CATCCTGATGTCGCAGCAGAAATTAAGAGATGGGGCACTTGGTATGCCAATGAACTGCAA
 H  P  D  V  A  A  E  I  K  R  W  G  T  W  Y  A  N  E  L  Q
205
       1150      1160      1170      1180      1190      1200
TTGGACGGTTTCCGTCTTGATGCTGTCAAACACATTAAATTTTCTTTTTTGCGGGATTGG
 L  D  G  F  R  L  D  A  V  K  H  I  K  F  S  F  L  R  D  W
225
       1210      1220      1230      1240      1250      1260
GTTAATCATGTCAGGGAAAAAACGGGGAAGGAAATGTTTACGGTAGCTGAATATTGGCAG
 V  N  H  V  R  E  K  T  G  K  E  M  F  T  V  A  E  Y  W  Q
245
       1270      1280      1290      1300      1310      1320
AATGACTTGGGCGCGCTGGAAAACTATTTGAACAAAACAAATTTTAATCATTCAGTGTTT
 N  D  L  G  A  L  E  N  Y  L  N  K  T  N  F  N  H  S  V  F
265
       1330      1340      1350      1360      1370      1380
GACGTGCCGCTTCATTATCAGTTCCATGCTGCATCGACACAGGGAGGCGGCTATGATATG
 D  V  P  L  H  Y  Q  F  H  A  A  S  T  Q  G  G  G  Y  D  M
285
       1390      1400      1410      1420      1430      1440
AGGAAATTGCTGAACGGTACGGTCGTTTCCAAGCATCCGTTGAAATCGGTTACATTTGTC
 R  K  L  L  N  G  T  V  V  S  K  H  P  L  K  S  V  T  F  V
305
       1450      1460      1470      1480      1490      1500
GATAACCATGATACACAGCCGGGGCAATCGCTTGAGTCGACTGTCCAAACATGGTTTAAG
 D  N  H  D  T  Q  P  G  Q  S  L  E  S  T  V  Q  T  W  F  K
325
       1510      1520      1530      1540      1550      1560
CCGCTTGCTTACGCTTTTATTCTCACAAGGGAATCTGGATACCCTCAGGTTTTCTACGGG
 P  L  A  Y  A  F  I  L  T  R  E  S  G  Y  P  Q  V  F  Y  G
345
       1570      1580      1590      1600      1610      1620
GATATGTACGGGACGAAAGGAGACTCCCAGCGCGAAATTCCTGCCTTGAAACACAAAATT
 D  M  Y  G  T  K  G  D  S  Q  R  E  I  P  A  L  K  H  K  I
365
       1630      1640      1650      1660      1670      1680
GAACCGATCTTAAAAGCGAGAAAACAGTATGCGTACGGAGCACAGCATGATTATTTCGAC
 E  P  I  L  K  A  R  K  Q  Y  A  Y  G  A  Q  H  D  Y  F  D
385
       1690      1700      1710      1720      1730      1740
CACCATGACATTGTCGGCTGGACAAGGGAAGGCGACAGCTCGGTTGCAAATTCAGGTTTG
 H  H  D  I  V  G  W  T  R  E  G  D  S  S  V  A  N  S  G  L
405
       1750      1760      1770      1780      1790      1800
GCGGCATTAATAACAGACGGACCCGGTGGGGCAAAGCGAATGTATGTCGGCCGGCAAAAC
 A  A  L  I  T  D  G  P  G  G  A  K  R  M  Y  V  G  R  Q  N
425
```

FIG.2B

```
       1810      1820      1830      1840      1850      1860
GCCGGTGAGACATGGCATGACATTACCGGAAACCGTTCGGAGCCGGTTGTCATCAATTCG
 A   G   E   T   W   H   D   I   T   G   N   R   S   E   P   V   V   I   N   S
445
       1870      1880      1890      1900      1910      1920
GAAGGCTGGGGAGAGTTTCACGTAAACGGCGGGTCGGTTTCAATTTATGTTCAAAGATAG
 E   G   W   G   E   F   H   V   N   G   G   S   V   S   I   Y   V   Q   R
465                                                                      483
       1930      1940      1950      1960      1970      1980
AAGAGCAGAGAGGACGGATTTCCTGAAGGAAATCCGTTTTTTTATTTTGCCCGTCTTATA 1990      2000      2010      2020      2030      2040
AATTTCTTTGATTACATTTTATAATTAATTTTAACAAAGTGTCATCAGCCCTCAGGAAGG 2050      2060      2070      2080      2090      2100
ACTTGCTGACAGTTTGAATCGCATAGGTAAGGCGGGGATGAAATGGCAACGTTATCTGAT 2110      2120      2130      2140
GTAGCAAAGAAAGCAAATGTGTCGAAAATGACGGTATCGCGGGTGATCA
```

FIG.2C

```
        10        20        30        40        50        60
AATTCACCTCGAAAGCAAGCTGATAAACCGATACAATTAAAGGCTCCTTTTGGAGCCTTT 70        80        90       100       110       120
TTTTTTGGAGATTTTCAACGTGAAAAAATTATTATTCGCAATTCCAAGCTAATTCACCTC 130       140       150       160       170       180
GAAAGCAAGCTGATAAACCGATACAATTAAAGGCTCCTTTTGGAGCCTTTTTTTTTGGAG 190       200       210       220       230       240
ATTTTCAACGTGAAAAAATTATTATTCGCAATTCCAAGCTCTGCCTCGCGCGTTTCGGTG 250       260       270       280       290       300
ATGACGGTGAAAACCTCTGACACATGCAGCTCCCGGAGACGGTCACAGCTTGTCTGTAAG 310       320       330       340       350       360
CGGATGCAGATCACGCGCCCTGTAGCGGCGCATTAAGCGCGGCGGGTGTGGTGGTTACGC 370       380       390       400       410       420
GCAGCGTGACCGCTACACTTGCCAGCGCCCTAGCGCCCGCTCCTTTCGCTTTCTTCCCTT 430       440       450       460       470       480
CCTTTCTCGCCACGTTCGCCGGCTTTCCCCGTCAAGCTCTAAATCGGGGGCTCCCTTTAG 490       500       510       520       530       540
GGTTCCGATTTAGTGCTTTACGGCACCTCGACCCCAAAAAACTTGATTAGGGTGATGGTT 550       560       570       580       590       600
CACGTAGTGGGCCATCGCCCTGATAGACGGTTTTTCGCCCTTTGACGTTGGAGTCCACGT 610       620       630       640       650       660
TCTTTAATAGTGGACTCTTGTTCCAAACTGGAACAACACTCAACCCTATCTCGGTCTATT 670       680       690       700       710       720
CTTTTGATTTATAAGGGATTTTGCCGATTTCGGCCTATTGGTTAAAAAATGAGCTGATTT 730       740       750       760       770       780
AACAAAAATTTAACGCGAATTTTAACAAAATATTAACGTTTACAATTTGATCTGCGCTCG 790       800       810       820       830       840
GTCGTTCGGCTGCGGCGAGCGGTATCAGCTCACTCAAAGGCGGTAATACGGTTATCCACA 850       860       870       880       890       900
GAATCAGGGGATAACGCAGGAAAGAACATGTGAGCAAAAGGCCAGCAAAAGGCCAGGAAC 910       920       930       940       950       960
CGTAAAAAGGCCGCGTTGCTGGCGTTTTTCCATAGGCTCCGCCCCCCTGACGAGCATCAC 970       980       990      1000      1010      1020
AAAAATCGACGCTCAAGTCAGAGGTGGCGAAACCCGACAGGACTATAAAGATACCAGGCG 1030      1040      1050      1060      1070      1080
TTTCCCCCTGGAAGCTCCCTCGTGCGCTCTCCTGTTCCGACCCTGCCGCTTACCGGATAC 1090      1100      1110      1120      1130      1140
CTGTCCGCCTTTCTCCCTTCGGGAAGCGTGGCGCTTTCTCAATGCTCACGCTGTAGGTAT
```

FIG.3A

```
      1150      1160      1170      1180      1190      1200
CTCAGTTCGGTGTAGGTCGTTCGCTCCAAGCTGGGCTGTGTGCACGAACCCCCCGTTCAG 1210      1220      1230      1240      1250      1260
CCCGACCGCTGCGCCTTATCCGGTAACTATCGTCTTGAGTCCAACCCGGTAAGACACGAC 1270      1280      1290      1300      1310      1320
TTATCGCCACTGGCAGCAGCCACTGGTAACAGGATTAGCAGAGCGAGGTATGTAGGCGGT 1330      1340      1350      1360      1370      1380
GCTACAGAGTTCTTGAAGTGGTGGCCTAACTACGGCTACACTAGAAGGACAGTATTTGGT 1390      1400      1410      1420      1430      1440
ATCTGCGCTCTGCTGAAGCCAGTTACCTTCGGAAAAAGAGTTGGTAGCTCTTGATCCGGC 1450      1460      1470      1480      1490      1500
AAACAAACCACCGCTGGTAGCGGTGGTTTTTTTGTTTGCAAGCAGCAGATTACGCGCAGA 1510      1520      1530      1540      1550      1560
AAAAAAGGATCTCAAGAAGATCCTTTGATCTTTTCTACGGGGTCTGACGCTCAGTGGAAC 1570      1580      1590      1600      1610      1620
GAAAACTCACGTTAAGGGATTTTGGTCATGAGATTATCAAAAAGGATCTTCACCTAGATC 1630      1640      1650      1660      1670      1680
CTTTTAAATTAAAAATGAAGTTTTAAATCAATCTAAAGTATATATGAGTAAACTTGGTCT 1690      1700      1710      1720      1730      1740
GACAGTTACCAATGCTTAATCAGTGAGGCACCTATCTCAGCGATCTGTCTATTTCGTTCA 1750      1760      1770      1780      1790      1800
TCCATAGTTGCCTGACTCCCCGTCGTGTAGATAACTACGATACGGGAGGGCTTACCATCT 1810      1820      1830      1840      1850      1860
GGCCCCAGTGCTGCAATGATACCGCGAGACCCACGCTCACCGGCTCCAGATTTATCAGCA 1870      1880      1890      1900      1910      1920
ATAAACCAGCCAGCCGGAAGGGCCGAGCGCAGAAGTGGTCCTGCAACTTTATCCGCCTCC 1930      1940      1950      1960      1970      1980
ATCCAGTCTATTAATTGTTGCCGGGAAGCTAGAGTAAGTAGTTCGCCAGTTAATAGTTTG 1990      2000      2010      2020      2030      2040
CGCAACGTTGTTGCCATTGCTGCAGGCATCGTGGTGTCACGCTCGTCGTTTGGTATGGCT 2050      2060      2070      2080      2090      2100
TCATTCAGCTCCGGTTCCCAACGATCAAGGCGAGTTACATGATCCCCCATGTTGTGCAAA 2110      2120      2130      2140      2150      2160
AAAGCGGTTAGCTCCTTCGGTCCTCCGATCGTTGTCAGAAGTAAGTTGGCCGCAGTGTTA 2170      2180      2190      2200      2210      2220
TCACTCATGGTTATGGCAGCACTGCATAATTCTCTTACTGTCATGCCATCCGTAAGATGC 2230      2240      2250      2260      2270      2280
```

FIG.3B

```
TTTTCTGTGACTGGTGAGTACTCAACCAAGTCATTCTGAGAATAGTGTATGCGGCGACCG
         2290      2300      2310      2320      2330      2340
AGTTGCTCTTGCCCGGCGTCAACACGGGATAATACCGCGCCACATAGCAGAACTTTAAAA
         2350      2360      2370      2380      2390      2400
GTGCTCATCATTGGAAAACGTTCTTCGGGGCGAAAACTCTCAAGGATCTTACCGCTGTTG
         2410      2420      2430      2440      2450      2460
AGATCCAGTTCGATGTAACCCACTCGTGCACCCAACTGATCTTCAGCATCTTTTACTTTC
         2470      2480      2490      2500      2510      2520
ACCAGCGTTTCTGGGTGAGCAAAAACAGGAAGGCAAAATGCCGCAAAAAAGGGAATAAGG
         2530      2540      2550      2560      2570      2580
GCGACACGGAAATGTTGAATACTCATACTCTTCCTTTTTCAATATTATTGAAGCAGACAG
         2590      2600      2610      2620      2630      2640
TTTTATTGTTCATGATGATATATTTTTATCTTGTGCAATGTAACATCAGAGATTTTGAGA
         2650      2660      2670      2680      2690      2700
CACAACGTGGCTTTGTTGAATAAATCGAACTTTTGCTGAGTTGACTCCCCGCGCGCGATG
         2710      2720      2730      2740      2750      2760
GGTCGAATTTGCTTTCGAAAAAAAAGCCCGCTCATTAGGCGGGCTAAAAAAAAAGCCCGCT
         2770      2780      2790      2800      2810      2820
CATTAGGCGGGCTCGAATTTCTGCCATTCATCCGCTTATTATCACTTATTCAGGCGTAGC
         2830      2840      2850      2860      2870      2880
AACCAGGCGTTTAAGGGCACCAATAACTGCCTTAAAAAAATTACGCCCCGCCCTGCCACT
         2890      2900      2910      2920      2930      2940
CATCGCAGTACTGTTGTAATTCATTAAGCATTCTGCCGACATGGAAGCCATCACAGACGG
         2950      2960      2970      2980      2990      3000
CATGATGAACCTGAATCGCCAGCGGCATCAGCACCTTGTCGCCTTGCGTATAATATTTGC
         3010      3020      3030      3040      3050      3060
CCATAGTGAAAACGGGGGCGAAGAAGTTGTCCATATTCGCCACGTTTAAATCAAAACTGG
         3070      3080      3090      3100      3110      3120
TGAAACTCACCCAGGGATTGGCTGAGACGAAAAACATATTCTCAATAAACCCTTTAGGGA
         3130      3140      3150      3160      3170      3180
AATAGGCCAGGTTTTCACCGTAACACGCCACATCTTGCGAATATATGTGTAGAAACTGCC
         3190      3200      3210      3220      3230      3240
GGAAATCGTCGTGGTATTCACTCCAGAGCGATGAAAACGTTTCAGTTTGCTCATGGAAAA
         3250      3260      3270      3280      3290      3300
CGGTGTAACAAGGGTGAACACTATCCCATATCACCAGCTCACCGTCTTTCATTGCCATAC
         3310      3320      3330      3340      3350      3360
GAAATTCCGGATGAGCATTCATCAGGCGGGCAAGAATGTGAATAAAGGCCGGATAAAACT
```

FIG.3C

```
           3370      3380      3390      3400      3410      3420
     TGTGCTTATTTTTCTTTACGGTCTTTAAAAAGGCCGTAATATCCAGCTAAACGGTCTGGT 3430      3440      3450      3460      3470      3480
     TATAGGTACATTGAGCAACTGACTGAAATGCCTCAAAATGTTCTTTACGATGCCATTGGG 3490      3500      3510      3520      3530      3540
     ATATATCAACGGTGGTATATCCAGTGATTTTTTTCTCCATTTTAGCTTCCTTAGCTCCTG 3550      3560      3570      3580      3590      3600
     AAAATCTCGATAACTCAAAAAATACGCCCGGTAGTGATCTTATTTCATTATGGTGAAAGT 3610      3620      3630      3640      3650      3660
     TGGAACCTCTTACGTGCCGATCAACGTCTCATTTTCGCCAAAAGTTGGCCCAGGGCTTCC 3670      3680      3690      3700      3710      3720
     CGGTATCAACAGGGACACCAGGATTTATTTATTCTGCGAAGTGATCTTCCGTCACAGGTA 3730      3740      3750      3760      3770      3780
     TTTATTCGAAGACGAAAGGGCATCGCGCGCGGGGAATTCGAGCTCGAGCTTACTCCCCAT 3790      3800      3810      3820      3830      3840
     CCCCCTGTTGACAATTAATCATCGGCTCGTATAATGTGTGGAATTGTGAGCGGATAACAA 3850      3860      3870      3880      3890      3900
     TTTCACACAGGAAACAGGATCCAAGGAGGTGATCTAGAGTCATGAAACAACAAAAACGGC
                                                M   K   Q   Q   K   R 3910      3920      3930      3940      3950      3960
     TTTACGCCCGATTGCTGACGCTGTTATTTGCGCTCATCTTCTTGCTGCCTCATTCTGCAG
      L   Y   A   R   L   L   T   L   L   F   A   L   I   F   L   L   P   H   S   A 3970      3980      3990      4000      4010      4020
     CAGCGGCGGCAAATCTTAATGGGACGCTGATGCAGTATTTTGAATGGTACATGCCCAATG
      A   A   A   A   N   L   N   G   T   L   M   Q   Y   F   E   W   Y   M   P   N
              +1
           4030      4040      4050      4060      4070      4080
     ACGGCCAACATTGGAAGCGTTTGCAAAACGACTCGGCATATTTGGCTGAACACGGTATTA
      D   G   Q   H   W   K   R   L   Q   N   D   S   A   Y   L   A   E   H   G   I
     18
           4090      4100      4110      4120      4130      4140
     CTGCCGTCTGGATTCCCCCGGCATATAAGGGAACTAGTCAAGCGGATGTGGGCTACGGTG
      T   A   V   W   I   P   P   A   Y   K   G   T   S   Q   A   D   V   G   Y   G
     38
           4150      4160      4170      4180      4190      4200
     CTTACGACCTTTATGATTTAGGGGAGTTTCATCAAAAAGGGACGGTTCGGACAAAGTACG
      A   Y   D   L   Y   D   L   G   E   F   H   Q   K   G   T   V   R   T   K   Y
     58
           4210      4220      4230      4240      4250      4260
     GCACAAAAGGAGAGCTGCAATCTGCGATCAAAAGTCTTCATTCCCGCGACATTAACGTTT
      G   T   K   G   E   L   Q   S   A   I   K   S   L   H   S   R   D   I   N   V
     78
           4270      4280      4290      4300      4310      4320
     ACGGGGATGTGGTCATCAACCACAAAGGCGGCGCTGATGCGACCGAAGATGTAACCGCGG
      Y   G   D   V   V   I   N   H   K   G   G   A   D   A   T   E   D   V   T   A
     98
```

FIG.3D

```
           4330      4340      4350      4360      4370      4380
TTGAAGTCGATCCCGCTGACCGCAACCGCGTAATTTCAGGAGAACACCTAATTAAAGCCT
 V  E  V  D  P  A  D  R  N  R  V  I  S  G  E  H  L  I  K  A
118
           4390      4400      4410      4420      4430      4440
GGACACATTTTCATTTTCCGGGGCGCGGCAGCACATACAGCGATTTTAAATGGCATTGGT
 W  T  H  F  H  F  P  G  R  G  S  T  Y  S  D  F  K  W  H  W
138
           4450      4460      4470      4480      4490      4500
ACCATTTTGACGGAACCGATTGGGACGAGTCCCGAAAGCTGAACCGCATCTATAAGTTTC
 Y  H  F  D  G  T  D  W  D  E  S  R  K  L  N  R  I  Y  K  F
158
           4510      4520      4530      4540      4550      4560
AAGGAAAGGCTTGGGATTGGAAGTTTCCAATGAAAACGGCAACTATGATTATTTGATGT
 Q  G  K  A  W  D  W  E  V  S  N  E  N  G  N  Y  D  Y  L  M
178
           4570      4580      4590      4600      4610      4620
ATGCCGACATCGATTATGACCATCCTGATGTCGCAGCAGAAATTAAGAGATGGGGCACTT
 Y  A  D  I  D  Y  D  H  P  D  V  A  A  E  I  K  R  W  G  T
198
           4630      4640      4650      4660      4670      4680
GGTATGCCAATGAACTGCAATTGGACGGTTTCCGTCTTGATGCTGTCAAACACATTAAAT
 W  Y  A  N  E  L  Q  L  D  G  F  R  L  D  A  V  K  H  I  K
218
           4690      4700      4710      4720      4730      4740
TTTCTTTTTTGCGGGATTGGGTTAATCATGTCAGGGAAAAAACGGGGAAGGAAATGTTTA
 F  S  F  L  R  D  W  V  N  H  V  R  E  K  T  G  K  E  M  F
238
           4750      4760      4770      4780      4790      4800
CGGTAGCTGAATATTGGCAGAATGACTTGGGCGCCCTGGAAAACTATTTGAACAAAACAA
 T  V  A  E  Y  W  Q  N  D  L  G  A  L  E  N  Y  L  N  K  T
258
           4810      4820      4830      4840      4850      4860
ATTTTAATCATTCAGTGTTTGACGTGCCGCTTCATTATCAGTTCCATGCTGCATCGACAC
 N  F  N  H  S  V  F  D  V  P  L  H  Y  Q  F  H  A  A  S  T
278
           4870      4880      4890      4900      4910      4920
AGGGAGGCGGCTATGATATGAGGAAATTGCTGAACGGTACGGTCGTTTCCAAGCATCCGT
 Q  G  G  G  Y  D  M  R  K  L  L  N  G  T  V  V  S  K  H  P
298
           4930      4940      4950      4960      4970      4980
TGAAATCGGTTACATTTGTCGATAACCATGATACACAGCCGGGGCAATCGCTTGAGTCGA
 L  K  S  V  T  F  V  D  N  H  D  T  Q  P  G  Q  S  L  E  S
318
           4990      5000      5010      5020      5030      5040
CTGTCCAAACATGGTTTAAGCCGCTTGCTTACGCTTTTATTCTCACAAGGGAATCTGGAT
 T  V  Q  T  W  F  K  P  L  A  Y  A  F  I  L  T  R  E  S  G
338
           5050      5060      5070      5080      5090      5100
ACCCTCAGGTTTTCTACGGGGATATGTACGGGACGAAAGGAGACTCCCAGCGCGAAATTC
 Y  P  Q  V  F  Y  G  D  M  Y  G  T  K  G  D  S  Q  R  E  I
358
           5110      5120      5130      5140      5150      5160
CTGCCTTGAAACACAAAATTGAACCGATCTTAAAAGCGAGAAAACAGTATGCGTACGGAG
 P  A  L  K  H  K  I  E  P  I  L  K  A  R  K  Q  Y  A  Y  G
378
```

FIG. 3E

```
        5170      5180      5190      5200      5210      5220
CACAGCATGATTATTTCGACCACCATGACATTGTCGGCTGGACAAGGGAAGGCGACAGCT
 A  Q  H  D  Y  F  D  H  H  D  I  V  G  W  T  R  E  G  D  S
398
        5230      5240      5250      5260      5270      5280
CGGTTGCAAATTCAGGTTTGGCGGCATTAATAACAGACGGACCCGGTGGGGCAAAGCGAA
 S  V  A  N  S  G  L  A  A  L  I  T  D  G  P  G  G  A  K  R
418
        5290      5300      5310      5320      5330      5340
TGTATGTCGGCCGGCAAAACGCCGGTGAGACATGGCATGACATTACCGGAAACCGTTCGG
 M  Y  V  G  R  Q  N  A  G  E  T  W  H  D  I  T  G  N  R  S
438
        5350      5360      5370      5380      5390      5400
AGCCGGTTGTCATCAATTCGGAAGGCTGGGGAGAGTTTCACGTAAACGGCGGGTCGGTTT
 E  P  V  V  I  N  S  E  G  W  G  E  F  H  V  N  G  G  S  V
458
        5410      5420      5430      5440      5450      5460
CAATTTATGTTCAAAGATAGGTGACCAGAGAGGACGGATTTCCTGAAGGAAATCCGTTTT
 S  I  Y  V  Q  R
478
        5470      5480      5490      5500      5510      5520
TTTATTTTGCCCGTCTTATAAATTTCTTTGATTACATTTTATAATTAATTTTAACAAAGT 5530      5540      5550      5560      5570      5580
GTCATCAGCCCTCAGGAAGGACTTGCTGACAGTTTGAATCGCATAGGTAAGGCGGGGATG 5590      5600      5610      5620      5630      5640
AAATGGCAACGTTATCTGATGTAGCAAAGAAAGCAAATGTGTCGAAAATGACGGTATCGC 5650      5660      5670
GGGTGATCCTCTAGAAGAAGCTTGGTCTAGAGGTCGA
```

FIG.3F

EcoR1

GAATTCGAGCTCGAGCTTACTCCCCATCCCCCTGTTGACAATTAATCATCGGCTCGTATA
                                              BamHI

ATGTGTGGAATTGTGAGCGGATAACAATTTCACACAGGAAACAGGATCCGCGGATCCGTG

------>phoA
GAGAAAATAAA GTGAAACAAAGCACTATTGCACTGGCACTCTTACCGTTACTGTTTACC
            M  K  Q  S  T  I  A  L  A  L  L  P  L  L  F  T CCTGTGACAAAAGCG GCAAAT
 P  V  T  K  A    A  N
              ------>amylase

FIG.8

MUTANT MICROBIAL α-AMYLASES WITH INCREASED THERMAL, ACID AND/OR ALKALINE STABILITY

TECHNICAL FIELD

The present invention relates to the field of genetic engineering and provides new DNA molecules comprising DNA sequences coding for enzymes with α-amylase activity. Specifically, mutant microbial α-amylases are disclosed having improved characteristics for use in the degradation of starch, in the desizing of textile and in other industrial processes. The disclosed α-amylases show increased thermal, acid and alkaline stability which makes them ideally suited for performing their activity under process conditions which could hitherto not be used.

BACKGROUND OF THE INVENTION

Starch consists of a mixture of amylose (15–30% w/w) and amylopectin (70–85% w/w). Amylose consists of linear chains of α-1,4-linked glucose units having a molecular weight (MW) from about 60,000 to about 800,000. Amylopectin is a branched polymer containing α-1,6 branch points every 24–30 glucose units, its MW may be as high as 100 million.

Sugars from starch, in the form of concentrated dextrose syrups, are currently produced by an enzyme catalyzed process involving: (1) liquefaction (or thinning) of solid starch with an α-amylase into dextrins having an average degree of polymerization of about 7–10, and (2) saccharification of the resulting liquefied starch (i.e. starch hydrolysate) with amyloglucosidase (also called glucoamylase or AG). The resulting syrup has a high glucose content. Much of the glucose syrup which is commercially produced is subsequently enzymatically isomerized to a dextrose/fructose mixture known as isosyrup.

α-Amylase (EC 3.2.1.1) hydrolyzes starch, glycogen and related polysaccharides by cleaving internal α-1,4-glucosidic bonds at random. This enzyme has a number of important commercial applications in, for example the sugar, brewing, alcohol and textile industry. α-Amylases are isolated from a wide variety of bacterial, fungal, plant and animal sources. The industrially most important α-amylases are those isolated from Bacilli.

In the first step of the starch degradation process, starch slurry is gelatinized by heating at relatively high temperature (up to 110° C.). The gelatinized starch is liquefied and dextrinized by a thermostable α-amylase in a continuous two stage process. The major process variables are starch concentration, α-amylase dose, temperature and pH. During the liquefaction-dextrinization reaction the process variables must be maintained within narrow limits to achieve good conversion ratios, since serious filtration problems may arise otherwise. See, for example, L. E. Coker and K. Venkatasubramanian, in: Biotechnology, p. 165–171, Ed. P. N. Cheremisinoff, P. B. Quellette, Technicom Publ. Corp. Lancaster Renn. 1985. One of the problems which frequently arises is the proper regulation of the temperature in the initial stage of the degradation process: overheating often causes denaturation of the α-amylase so that the final thinning is not sufficient. One way to avoid this is the use of more thermostable α-amylases.

To that end it has been proposed to add calcium ions or an amphiphile (see e.g. EP-A-0189838), but this solution appeared to be unsatisfactory.

There is, therefore, still substantial interest to provide α-amylases with increased thermostability.

Relevant Literature

EP-A-057976 describes the isolation of a thermostable α-amylase coding gene from *B. stearothermophilus* the gene is cloned into a plasmid containing either a Bacillus or an *E. coli* origin of replication. The so obtained chimeric plasmid is used for producing α-amylase. The α-amylase gene was isolated and used without any further modification.

EP-A-0134048 describes a method for increased commercial production inter alia of α-amylase, by cloning and expression of one or more α-amylase genes in industrial Bacillus strains.

EP-A-252666 describes a chimeric α-amylase with the general formula Q-R-L in which Q is a N-terminal polypeptide of 55 to 60 amino acid residues which is at least 75 percent homologous to the 37 N-terminal residues of the *B. amyloliquefaciens* α-amylase, R is a given polypeptide and L is a C-terminal polypeptide of 390 to 400 amino acid residues which is at least 75 percent homologous to the 395 C-terminal residues of *B. licheniformis* α-amylase.

Gray et al. (J. Bacteriol., 1986, 16.6, 635) describe chimeric α-amylases formed of the $NH_2$-terminal portion of *B. stearothermophilus* α-amylase and the COOH-terminal portion of *B. licheniformis* α-amylase. Most of the hybrid enzyme molecules were shown to be less stable than the parent wild-type enzymes. Furthermore none of the hybrid molecules was shown to possess improved stability properties.

None of the references cited above describes the use of single amino acid replacements to obtain novel α-amylases.

EP-A-0285123 discloses a method for complete mutagenesis of nucleic acid sequences. As an example mutagenesis of the *B. stearothermophilus* α-amylase is described. Although there is a suggestion that this method can be used to obtain *B. stearothermophilus* α-amylase mutants with improved stability no examples are given.

SUMMARY OF THE INVENTION

The present invention provides mutant α-amylases and ways of obtaining such mutants. Said mutant α-amylases are characterized in that they differ in at least one amino acid from the wild-type enzyme. Furthermore, DNAs encoding these mutants, vectors containing these DNAs in expressionable form and host cells containing these vectors are provided.

In one aspect of the invention random mutagenesis on cloned α-amylase genes is disclosed. The mutated genes are expressed in a suitable host organism using a suitable vector system.

In another aspect of the invention screening methods for mutant α-amylases are described and applied. Said methods yield more thermostable and more acid stable α-amylases. Furthermore, this method is used with a slight modification to obtain more alkaline stable α-amylases. The expression products of the clones so detected are isolated and purified.

In yet another aspect of the invention α-amylases are provided with increased thermostability, these mutant α-amylases reduce filtration problems under application conditions of starch degradation.

In a further aspect of the invention α-amylases are provided with increased acid stability, these reduce the formation of unfavourable by-products, such as maltulose, at the same time they decrease the amount of acid to be added before the reaction with amyloglucosidase. The new α-amylases possess preferably both improved properties with respect to thermostability and acid stability or with respect to both thermostability and alkaline stability.

In another aspect of the invention the mutant proteins are shown to have a better performance under application conditions of starch liquefaction. The alkaline stability is especially useful for application in textile desizing.

These aspects will be further described in the detailed description and in the examples hereinafter.

BRIEF DESCRIPTION OF THE DRAWINGS

FIG. 1A–D: Nucleotide sequence of pMa5–8 (SEQ ID NO: 1)

Stanssens et al., 1987, EMBO Laboratory Course Martinsried, July 1987. For description of the different elements see text.

FIG. 2A–C: Nucleotide sequence of plasmid pPROM SPO2 insert (SEQ ID NO: 2)

Construction of this vector has been described in EP-A0224294. The α-amylase amino acid sequence is depicted below the triplets. Numbering starts from the first amino acid of the mature protein (Kuhn et al., 1982, J. Bacteriol, 149, 372). The SPO2 promoter insert runs from position 61 to 344.

FIG. 3A–F: Nucleotide sequence of pMaTLia6 (SEQ ID NO: 4)

This vector was constructed from pMa5–8, the insert of pPROM SPO2 and a synthetic DNA fragment encoding the TAC promoter. The TAC promoter DNA fragment runs from position 3757 to position 3859. The α-amylase amino acid sequence is depicted below the triplets.

Figure 4:
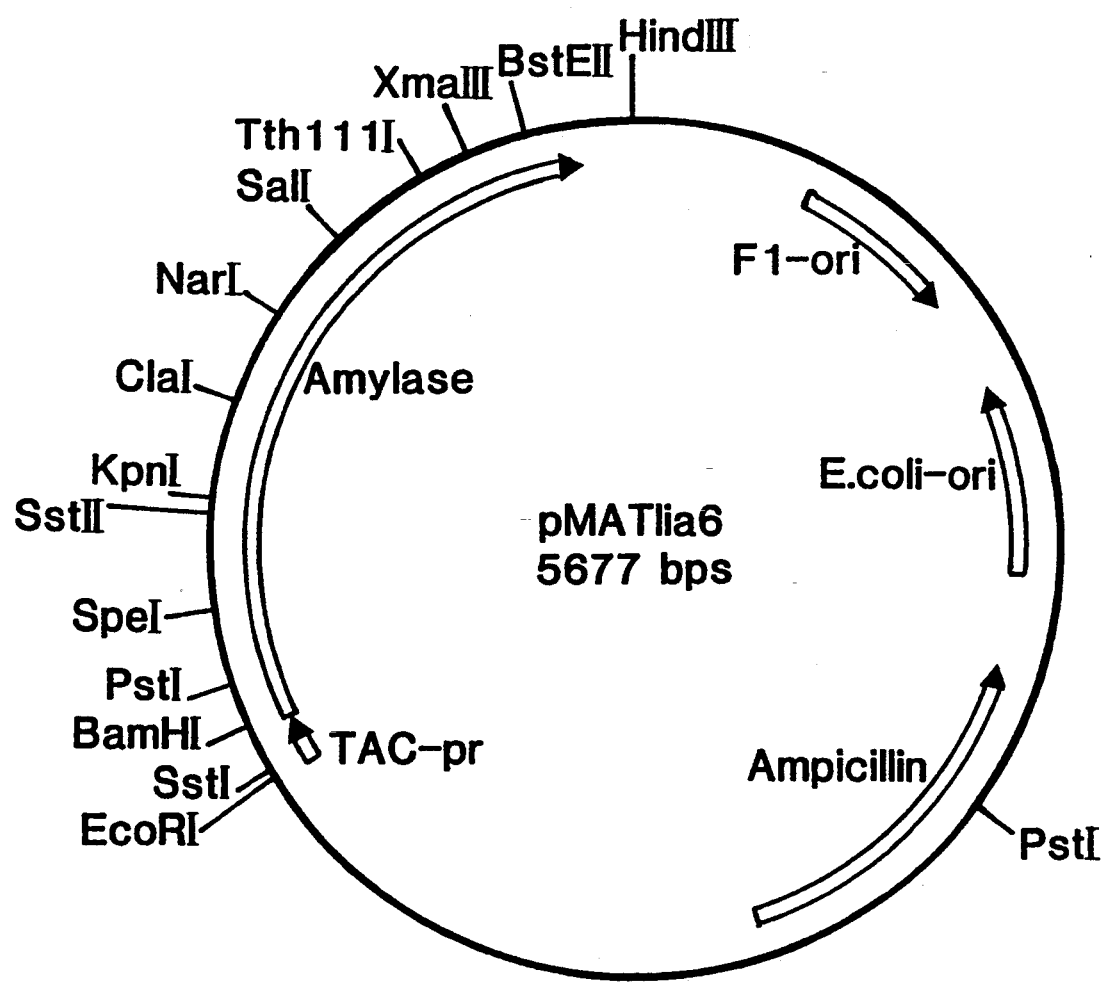

FIG. 4: Restriction map of pMaTLia6

The following unique restriction enzyme sites are available for gap construction in the α-amylase gene: BamHI, SpeI, SacII, KpnI, ClaI, NarI, SalI, Tht111I, XmaIII and BstEII. Sequencing primers for all possible gaps have been synthesized in order to enable easy determination of mutations. Plasmid pMcTLia6 is identical with pMaTLia6 except for the presence of an amber codon in the ampicillin gene (removes ScaI site) and the absence of an amber codon in the chloramphenicol gene (associated with the presence of a PvuII site).

Figure 5:
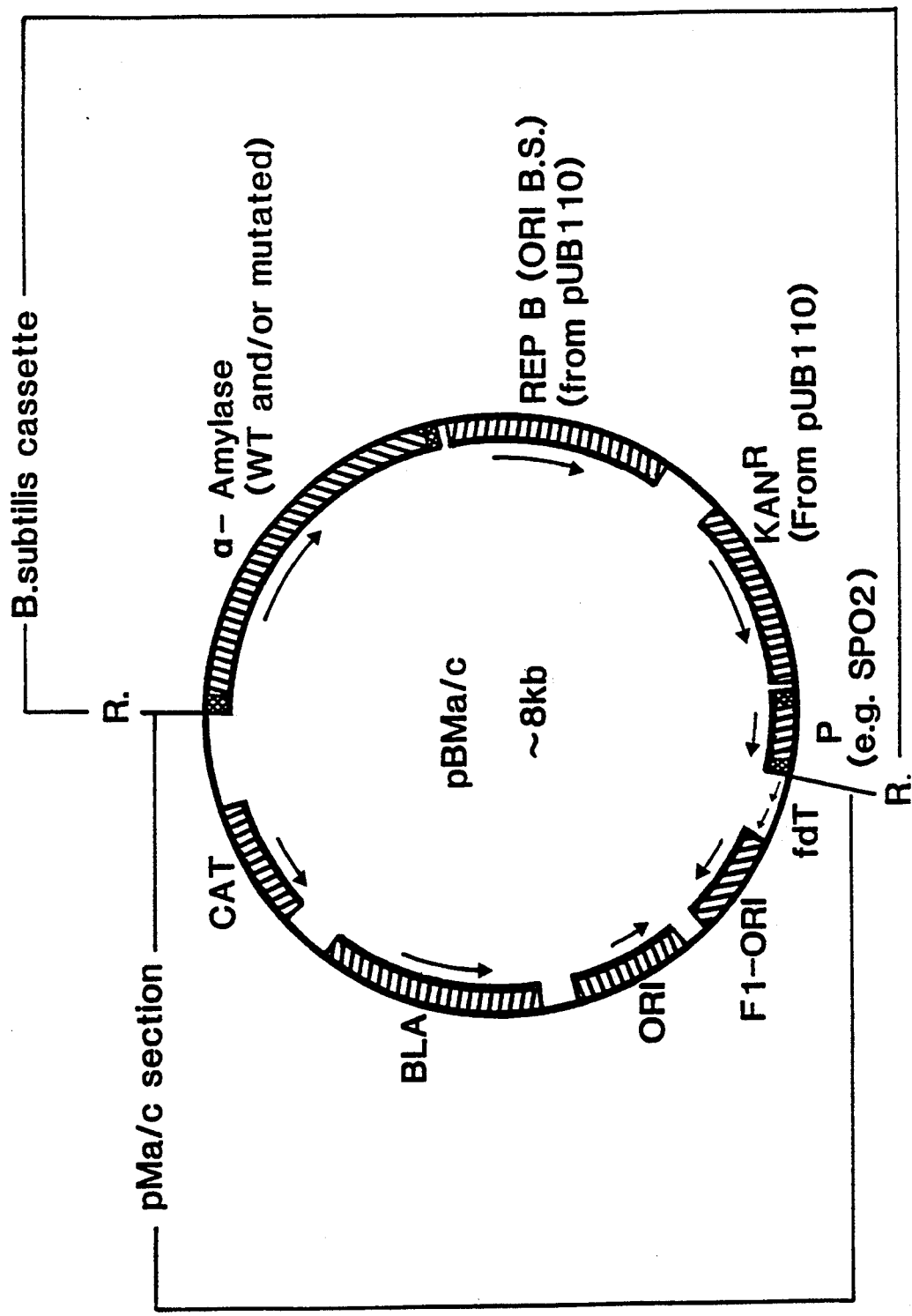

FIG. 5: Outline of Bacillus/E. coli shuttle vector pBMa/c

The (left) pMa/c section enables convenient mutagenesis in E. coli. The (right) Bacillus subtilis cassette contains the α-amylase gene (or any other Bacillus gene) plus a minimal replicon for propagation in B. subtilis. After successful mutagenesis in E. coli the B. subtilis cassette can be circularized allowing the SPO2 promoter to move in front of the α-amylase gene upon transformation into Bacillus.

Figure 6:
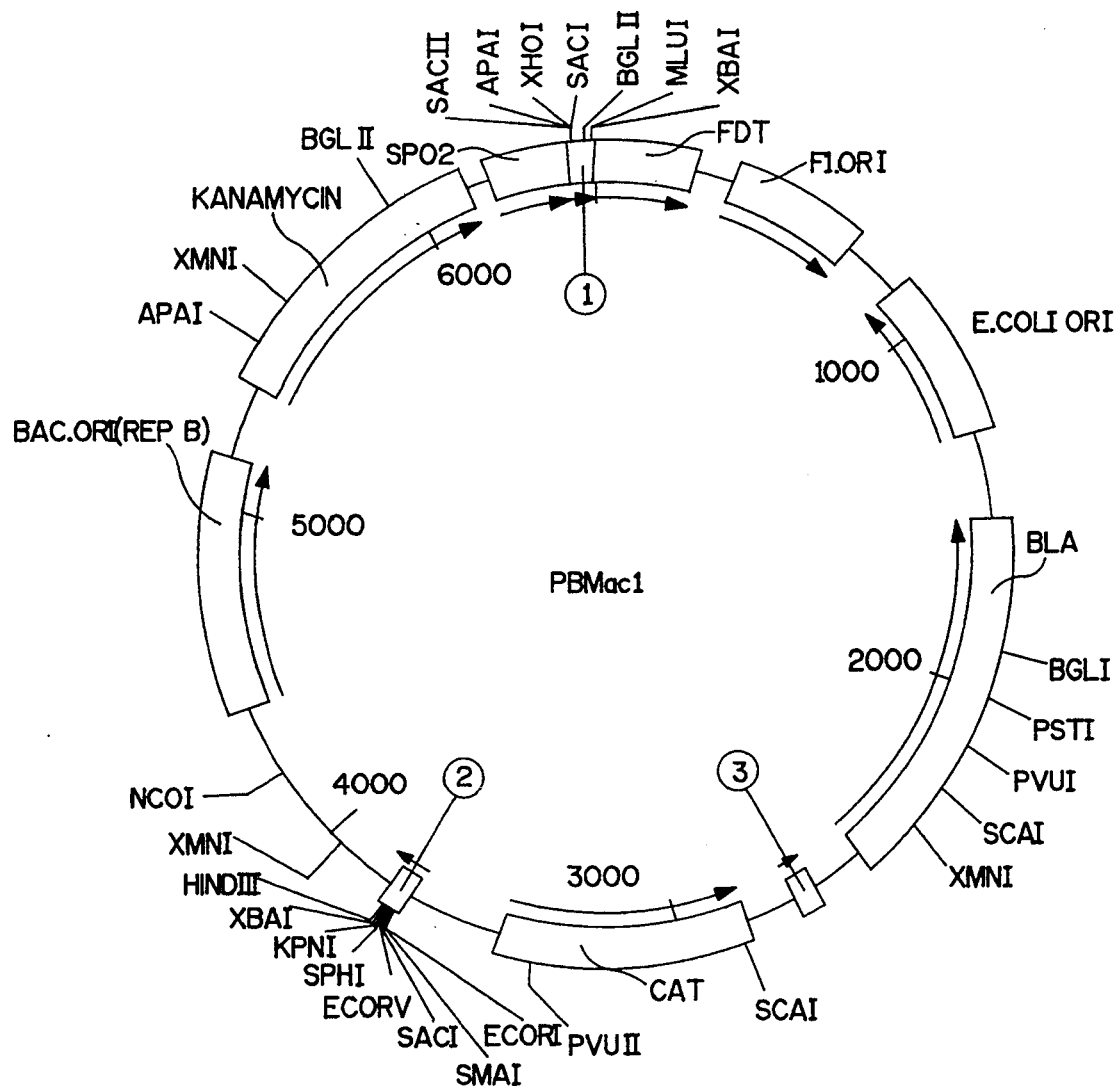

FIG. 6: Restriction map of pBMa/c1

This vector is a specific example of the mutagenesis expression vector outlined in FIG. 5.

(1) and (2): multiple cloning sites. The target gene is inserted in (2). By varying the sites at (1) and (2) convenient restriction sites for gapped duplex creation can be constructed;

FDT: transcription terminator

F1.ORI: origin of replication originating from phage F1

E. coli ORI: origin of replication from pBR322

BLA: ampicillin resistance gene

CAT: chloramphenicol resistance gene

BAC ORI: origin of replication of pUB110

KANAMYCIN: kanamycin (neomycin) resistance gene of pUB110

SPO2: promoter of phage SPO2

Figure 7:
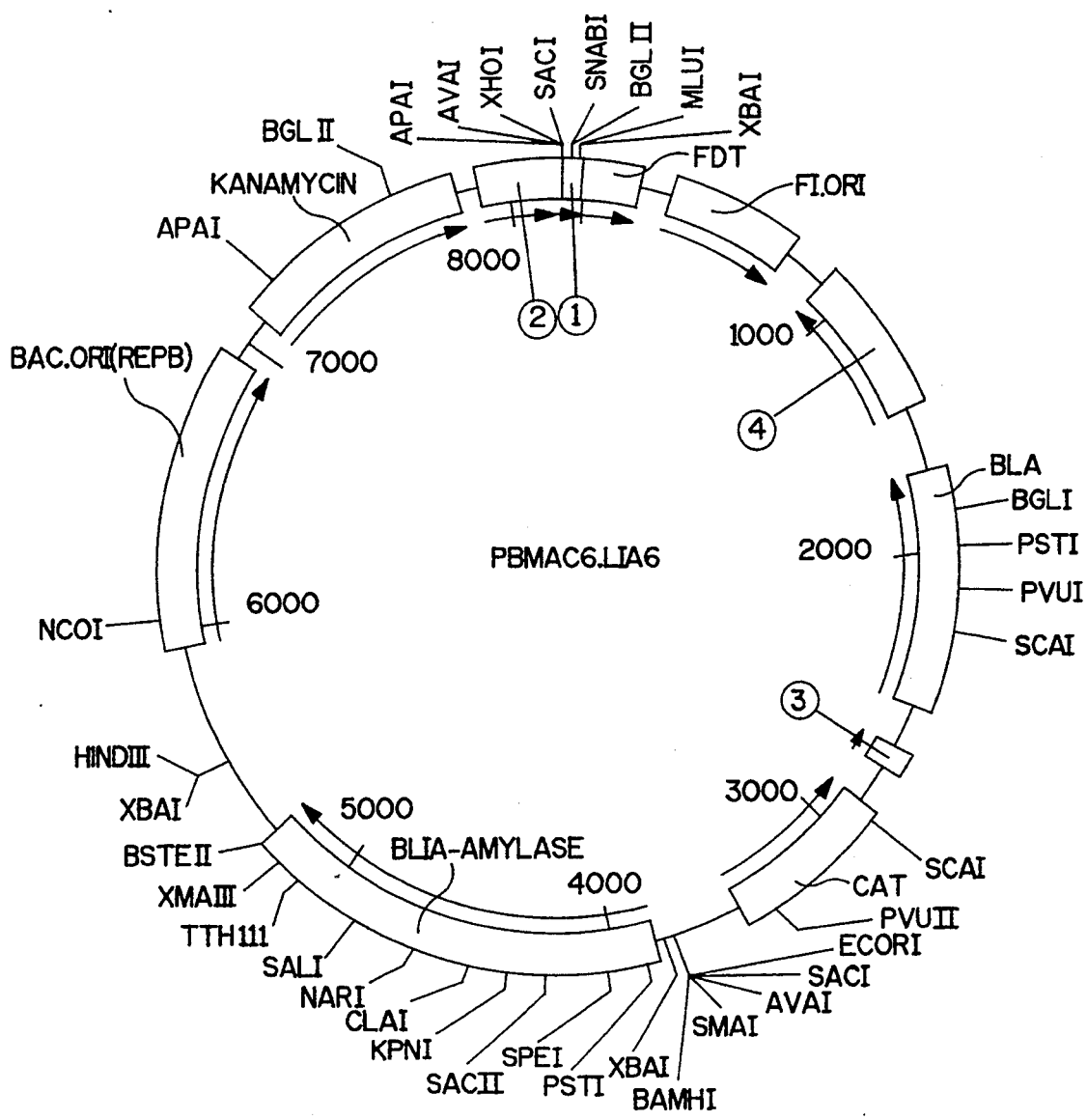

FIG. 7: Restriction map of pBMa/c6Lia6

The Bacillus licheniformis α-amylase gene was engineered into pBMa/c1 at multiple cloning site (2) of FIG. 6. In this figure the SPO2 promoter is indicated by (2) and the E. coli ORI is represented by (4).

FIG. 8: Sequence of phoA signal sequence fragment (SEQ ID NO: 6) in pMa/c TPLia6

Depicted is the sequence (SEQ ID NO: 7) from the EcoRI site upstream from the TAC-promoter up to the first amino acids of mature α-amylase. The phoA amino acid sequence is shown below the DNA sequence.

Figure 9:
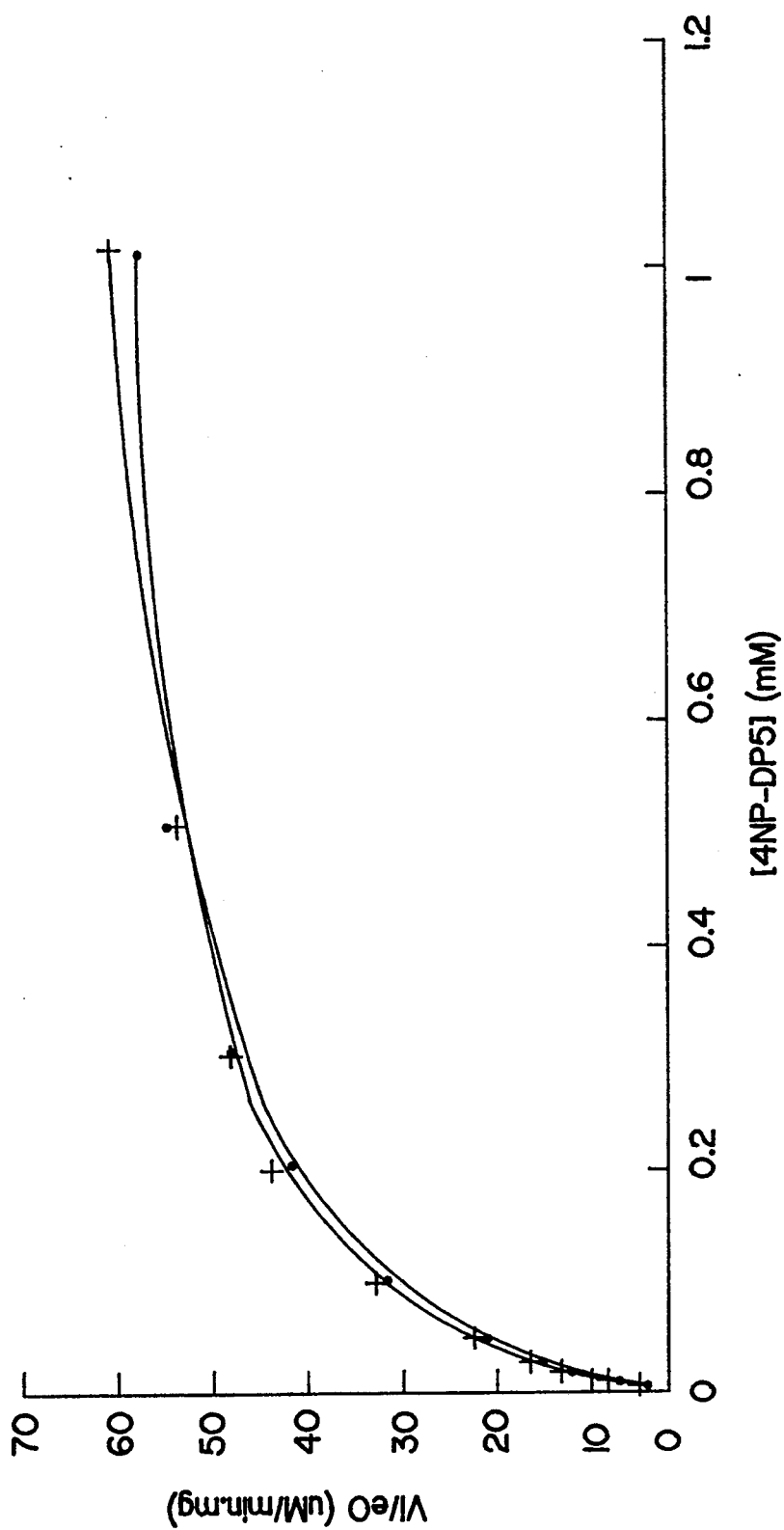

FIG. 9: Michaelis-Menten plot for WT and 2D5 α-amylase

This plot shows the initial rate of enzyme activities vs. substrate concentration for WT and 2D5 α-amylase. Assay conditions are described in Example 8.

Figure 10:
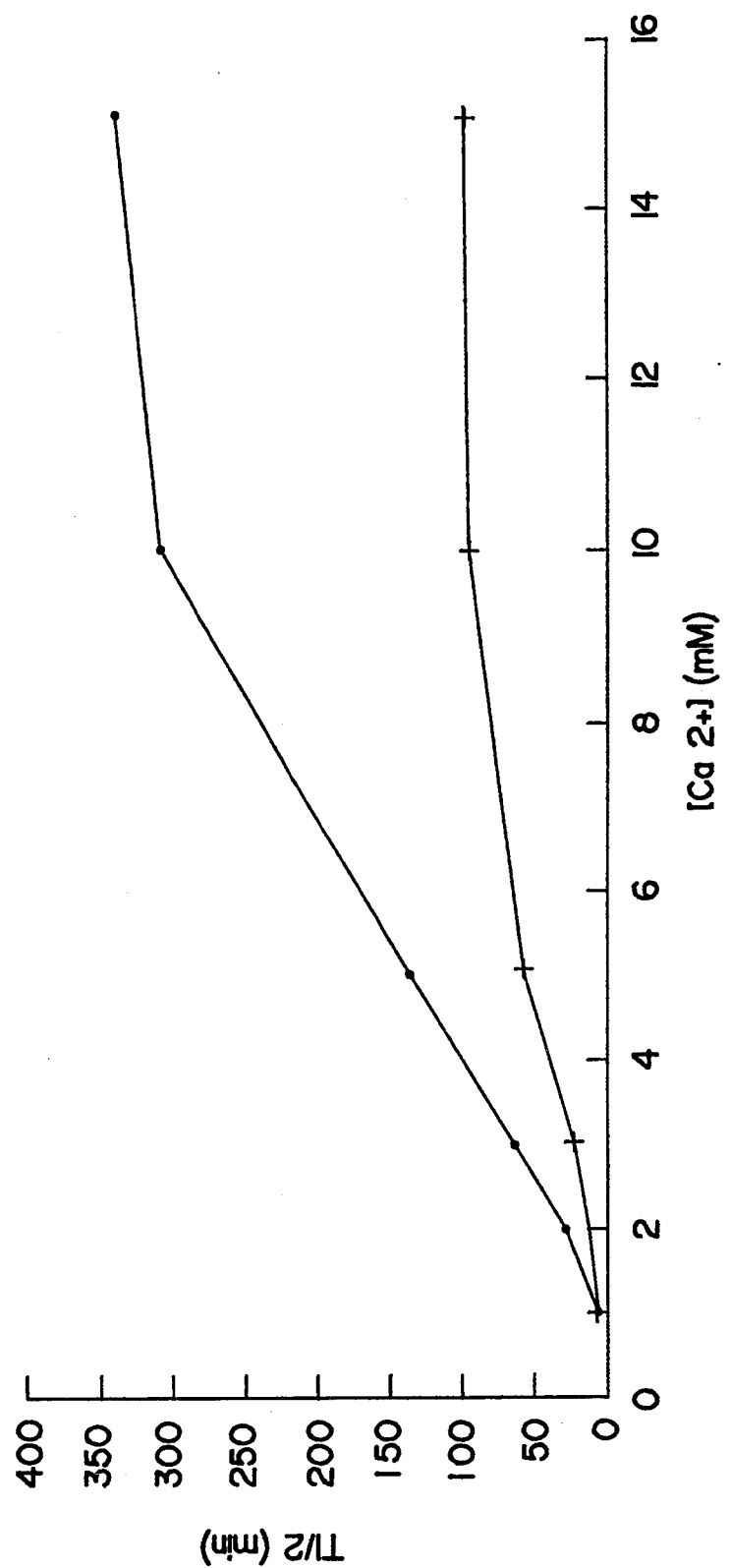

FIG. 10: Thermoinactivation of WT and D7 α-amylase

This plot shows the half life time of both WT and D7 α-amylase as a function of the $Ca^{2+}$ concentration at pH 5.5 and 90.5° C.

Figure 11:
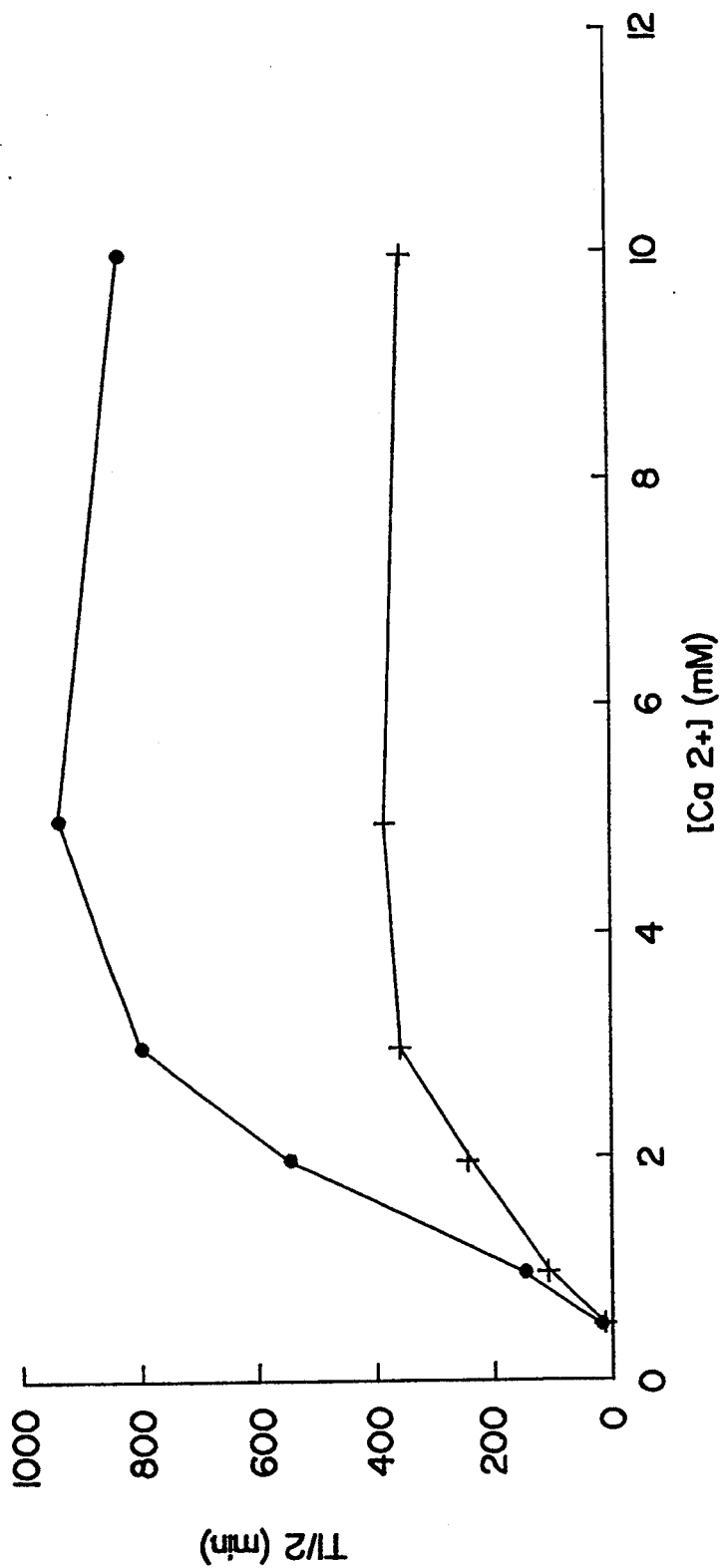

FIG. 11: Thermoinactivation of WT and D7 α-amylase

As in FIG. 10 except for the pH which is 7.0.

Figure 12:
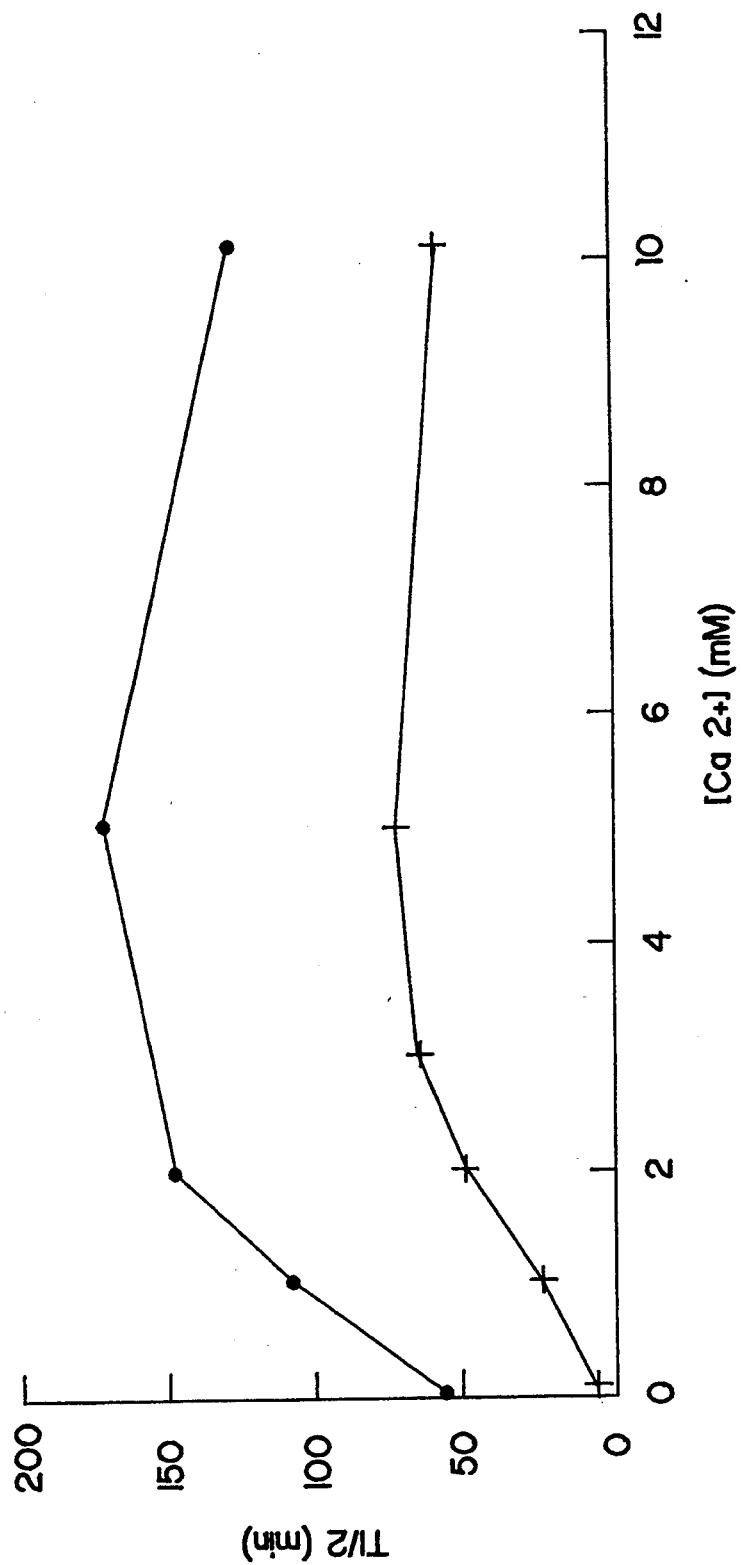

FIG. 12: Thermoinactivation of WT and 2D5 α-amylase

This plot shows half life times of both WT and 2D5 α-amylase as a function of $Ca^{2+}$ concentration at pH 7.0 and 95°C.

Figure 13:
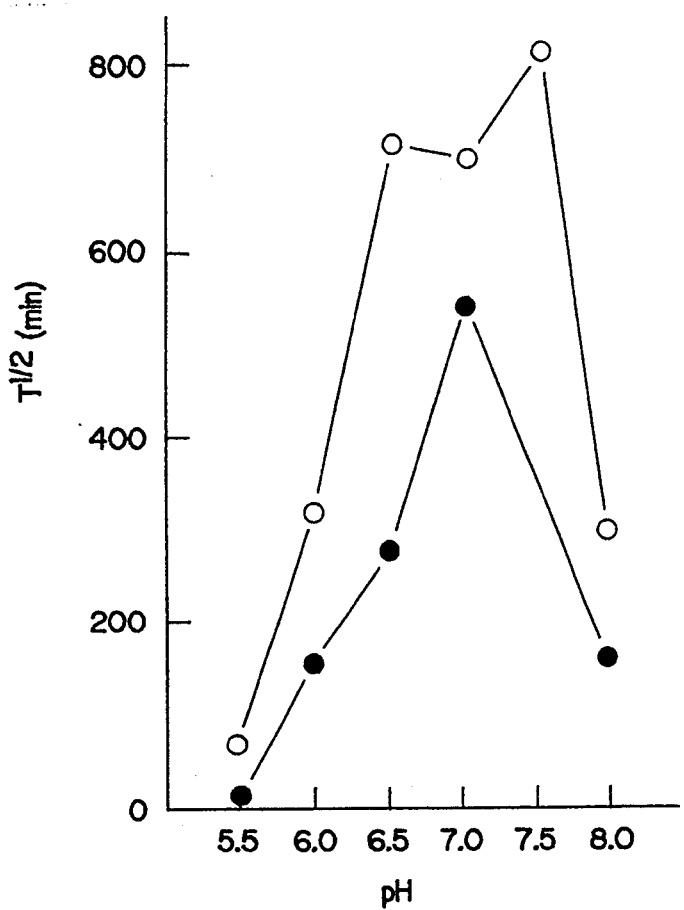

FIG. 13: Thermoinactivation of WT and D7 α-amylase as a function of pH

Figure 14:
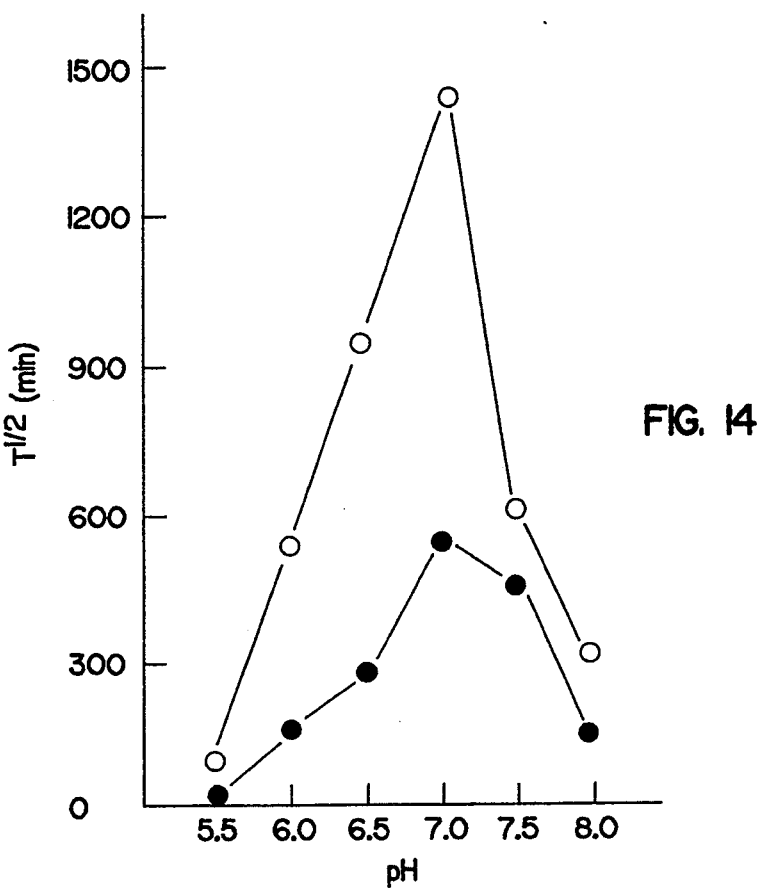

FIG. 14: Thermoinactivation of WT and 2D5 α-amylase as a function of pH

Figure 15:
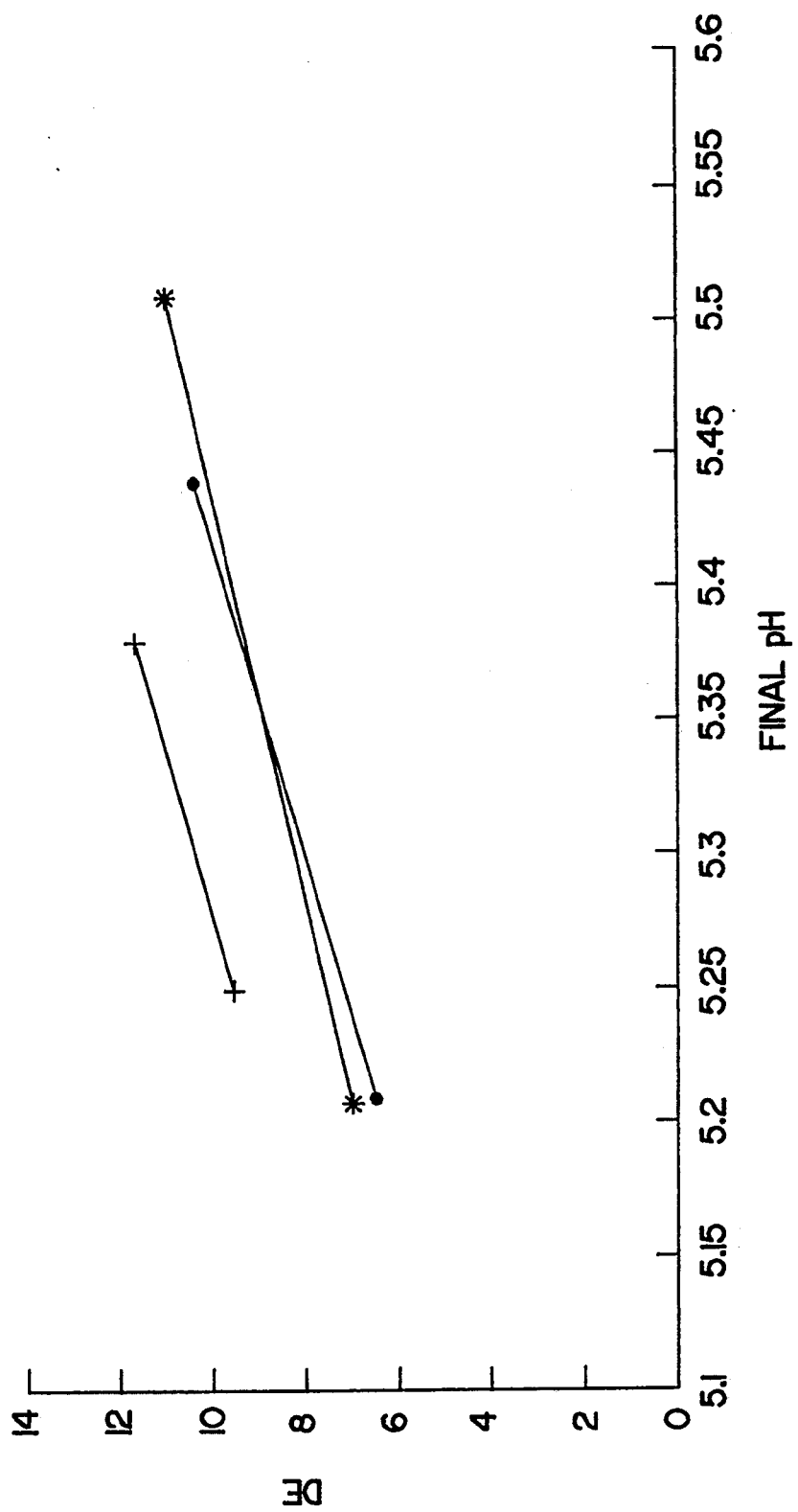

FIG. 15: DE vs final pH measured after liquefaction at 110° C.

DETAILED DESCRIPTION OF THE INVENTION

By the term "exhibits improved properties" as used in connection with "mutant α-amylase" in the present description we mean α-amylases which have a higher enzymatic activity or a longer half-life time under the application conditions of starch liquefaction, textile desizing and other industrial processes.

With "improved thermostability" we mean that the mutant enzyme retains its activity at a higher process temperature, or that it performs longer at the same temperature than the wild-type enzyme from which it originates.

With "improved acid (or alkaline) stability" we mean that the mutant enzyme performs better at lower (or higher) pH values then the wild-type enzyme from which it was derived.

It is to be understood that the improved properties are caused by the replacement of one or more amino acids.

Chromosomal DNA may be isolated from an α-amylase containing microorganism. Preferably a microorganism is used belonging to the genus Bacillus, more preferably *B. licheniformis*, still more preferably *B. licheniformis* T5 is used (see EP-A-134048). The chromosomal DNA is digested with a suitable restriction enzyme and cloned into a vector. A number of possible ways of selection can be used e.g. hybridization, immunological detection and detection of enzymatic activity. The choice of the vector used for cloning the digested chromosomal DNA will depend on the selection method available. If hybridization is used no special precautions are needed. However, if detection is immunological or based on enzymatic activity the vector will have to contain the proper expression signals. The actual detection of clones containing α-amylase was performed on starch containing agar plates. After growth and incubation with $I_2$ vapor halos are detected around positive clones. As a next step the sequence of the gene is determined. The derived amino acid sequence is used for comparison with other known α-amylase sequences to give a first impression of important amino acids (e.g. active-site, $Ca^{2+}$ binding, possible S-S bridges). A better indication is obtained when the 3D-structure is determined. Since this is very laborious oftentimes another approach is used. In the absence of a 3D-structure prediction programs for determining the secondary structural elements (e.g. α-helix, β-sheet) are successfully used eventually the tertiary structural elements e.g. β-barrel are determined. For a review see Janin, J. and Wodack, S. J., Prog. Biophys. molec. Biol. 1983, 42, 21–78.

Valuable amino acid replacements can be envisioned. The stability of a protein structure is determined by the net difference in free energy between the folded and unfolded conformations of the protein. Since the proline residue is restricted to fewer conformations than the other amino acids the configurational entropy of unfolding a protein is decreased (and stability thereby increased) when an amino acid is replaced with proline. Another useful substitution is the glycine to alanine replacement. Residues such as threonine, valine and isoleucine with branched β-carbons restrict the backbone conformation more than non-branched residues.

Since a part of the thermostability of certain proteins is due to salt bridges it may be advantageous to introduce lysine and arginine residues (Tomozic S. J. and Klibanov A. M., J. Biol. Chem., 1988, 263 3092–3096). Moreover replacement of lysine by arginine residues may improve the stability of salt bridges since arginine is able to form an additional H-bond. For a review see Wigby, D. B. et al. Biochem. Biophys. Res. Comm. 1987, 149, 927–929. Deamidation of asparagine and glutamine is mentioned to cause a serious disruption of the enzyme structure, replacement with non-amide residues may avoid this disruption. Amino acid replacements are best made by mutagenesis at the DNA level.

In principle mutagenesis experiments can be performed immediately on isolated clones. However, the insert is preferably cloned in a mutagenesis/expression vector. Random mutagenesis is possible and so is site-directed mutagenesis. In view of the huge amount of mutated clones of the former method, and since no 3D-structure of α-amylase is known to make possible an educated guess for site-directed mutagenesis we decided to perform "random" mutagenesis in specific regions.

The following is a possible approach for practising the present invention.

First the gene is modified by the introduction of "silent" restriction sites. Introduction of non-silent restriction sites is also possible. This makes possible the deletion of specific regions of the gene. Secondly the gene is cloned in a phasmid. This combination of a phage and a plasmid makes easy the production of single stranded DNA. Other ways of obtaining single stranded DNA are also possible. By hybridizing melted double-stranded vector (plus insert) DNA with a vector/insert combination containing a gap in the insert, gapped heteroduplex DNA was obtained (for a detailed description see Morinaga, Y et al. 1984, Biotechnology, 2, 636).

The gap is used for chemical or enzymatic mutagenesis. Preferably we used the bisulphite method (Folk and Hofstetter, Cell, 1983, 33, 585) and an enzymatical misincorporation method are used (modified version of Lehtovaara et al., Prot. Eng., 1988, 2, 63). These methods can be applied in such a way that every single nucleotide in the gap is replaced by all three other nucleotides (saturation mutagenesis). The latter method can be applied in several ways. In one of them a synthetic primer is hybridized to the gap. Subsequently an extension reaction is performed in which the deoxynucleotide complementary to the first deoxynucleotide 3' from the primer is missing. In principle all three of the other deoxynucleotides can thus be incorporated. This can be achieved either by using a mix of three deoxynucleotides or by using three separate reactions each containing only one deoxynucleotide. Another way of applying the method yields random clones. Here, four separate reactions are set up each of them containing one limiting deoxynucleotide. This gives second strands that stop before every single nucleotide. The subsequent steps can be performed as described above. Both the bisulphite and the enzymatic mutagenesis method were employed to obtain mutants.

For testing the enzymatic properties it may be convenient to express the cloned genes in the same host as that used during mutagenesis experiments. In principle this can be any host cell provided that suitable mutagenesis/expression vector systems for these cells are available. For the most part *E. coli* is very convenient to work with, for example *E. coli* WK6. After growth of the colonies in microtiterplates samples from the wells of these plates are spotted on agar plates supplemented with starch and buffered at different pH values. Positive clones can be detected by halo formation. Screening with appropriate buffers can be used to select for thermostability, acid stability, alkaline stability, saline stability or any other stability that can be screened for.

Suitable host strains for production of mutant α-amylases include transformable microorganisms in which the expression of α-amylase can be achieved. Specifically host strains of the same species or genus from which the α-amylase is derived, are suited, such as a Bacillus strain. Preferably an α-amylase negative Bacillus strain is used more preferably an α-amylase and protease negative Bacillus strain.

For example *B. licheniformis* T9 has been used to produce high amounts of mutant α-amylases.

Preferably, the α-amylases being produced are secreted into the culture medium (during fermentation), which facilitates their recovery. Any suitable signal sequence can be used to achieve secretion.

The expressed α-amylase is secreted from the cells and can be subsequently purified by any suitable method. Gelfiltration and Mono Q chromatography are examples of such methods. The isolated α-amylase was tested for thermo-inactivation at different $Ca^{2+}$ concentrations (0.5–15 mM) and over a wide pH range (5.5–8.0). Tests were also performed under application conditions. Specifically mutant α-amylase was tested under conditions of starch liquefaction at pH 5.5 and 5.25. Furthermore, applications for textile desizing have been tested.

The properties of some of the mutants that are screened will be better suited under the desired performance conditions.

The present invention discloses α-amylases with increased thermostability, improved acid stability and improved alkaline stability. Generally the number of amino acid replacements is not important as long as the activity of the mutated protein is the same or better than that of ther wild-type enzyme. Mutant α-amylases differ in at least one amino acid from the wild-type enzyme, preferably the mutants differ in from 1 to 10 amino acids. Specific mutants with improved properties include mutant α-amylases containing one or more amino acid replacements at the following positions 111, 133 and 149 (numbering is in accordance with the B. licheniformis α-amylase). Among the preferable amino and replacements are Ala-111-Thr, His-133-Tyr and Thr-149-Ile.

Such mutant enzymes show an improved performance at pH values below 6.5 and/or above 7.5. The performance is also increased at high temperatures leading to an increased half-life-time at for example temperatures of up to 110° C.

Many of the available α-amylase products are obtained from bacterial sources, in particular Bacilli, e.g. *B. subtilis, B. licheniformis, B. stearothermophilus, B. coagulans* and *B. amyloliquefaciens.* These enzymes show a high degree of homology and similarity (Yuuki et al., J. Biochem., 1985, 98, 1147; Nakajima et al., Appl. Microbiol. Biotechnol., 1986, 23, 355). Therefore knowledge of favourable mutations obtained from one of these α-amylases can be used to improve other amylases. The present invention provides an approach for obtaining such knowledge.

Following is a description of the experimental methods used and examples to illustrate the invention. The examples are only for illustrative purpose and are therefore in no way intended to limit the scope of the invention.

EXPERIMENTAL

Materials and Methods

1. General cloning techniques

Cloning techniques were used as described in the handbooks of T. Maniatis et al., 1982, Molecular Cloning, Cold Spring Harbor Laboratory; F. M. Ausubel et al., 1987, Current Protocols in Molecular Biology, John Wiley & Sons Inc., New York; B. Perbal, 1988, A practical Guide to Molecular Cloning, 2nd edition, John Wiley & Sons Inc., New York. These handbooks describe in detail the protocols for construction and propagation of recombinant DNA molecules, the procedures for making gene libraries, the procedures for sequencing and mutating DNA and the protocols for the enzymatic handling of DNA molecules. 2. Chemical mutagenesis Cloned DNA may be treated in vitro with chemicals in order to introduce mutations in the DNA. If these mutations are directed to amino acid encoding triplet codons a mutated protein can be produced by the mutated cloned DNA. A method for chemical mutagenesis with the aid of sodium bisulfite is described by Shortle and Botstein (Methods Enzymol., 1983, 100, 457). A preferable method is described by Folk and Hofstetter (Cell, 1983, 33, 585). Other methods for mutagenesis are described by Smith, Ann. Rev. Genet., 1985, 19, 423. A particularly useful protocol is described by Ausubel et al., ibid. 3. Mutagenesis on gapped-duplex DNA A method based on the gapped-duplex approach (Kramer et al., 1984, Nucl. Acids Res. 12, 9441) and a phasmid (plasmid/phage hybrid) was used. Essentially the method rests on a gapped duplex DNA intermediate consisting of a gapped strand (−strand) containing a wild-type antibiotic resistance marker and a template strand (+strand) carrying an amber mutation in the gene conferring resistance to the antibiotic. After annealing, the mutagenic oligonucleotide becomes incorporated in the gapped strand during in vitro gap-filling and sealing reaction. The resultant molecules are used to transform a mismatch repair deficient (Mut S) host in which the linkage between the intended mutation and the antibiotic resistance marker is preserved. The mixed phasmid population, isolated from this strain, is then allowed to segregate in a suppressor negative host strain. Transformants are plated on antibiotic containing medium, thus imposing a selection for progeny derived from the gapped strand.

The twin vector system pMa/c5–8, which was described by P. Stanssens et al. (Nucl. Acids Res., 1989, 17, 4441) is composed of the following elements:

pos 11–105: bacteriophage fd, terminator
pos 121–215: bacteriophage fd, terminator
pos 221–307: plasmid pBR322 (pos 2069–2153)
pos 313–768: bacteriophage f1, origin of replication (pos 5482–5943)
pos 772–2571: plasmid pBR322, origin of replication and β-lactamase gene
pos 2572–2685: transposon Tn903
pos 2519–2772: tryptophan terminator (double)
pos 2773–3729: transposon Tn9, chloramphenicol acetyl transferase gene
pos 3730–3803: multiple cloning site The sequence is depicted in FIG. 1 (SEQ ID NO: 1).

In the pMa type vector nucleotide 3409 is changed from G to A, while in the pMc type vector nucleotide 2238 is changed from G to C, creating amber stopcodons in the acetyl transferase gene and β-lactamase gene, respectively, rendering said genes inactive.

All sequences referred to were obtained from Genbank (TM) (release 54), National Nucleic Acid Sequence Data Bank, NIH USA. Plasmid pMc5–8 has been deposited under DSM 4566. To perform mutagenesis the target DNA fragment is cloned into the multiple cloning site of pMa5–8. Subsequently a gapped duplex between pMa5–8 containing the target DNA and pMc5–8 is constructed.

The single strand gap, consisting of the target DNA, can be subjected to mutagenesis with a mutagenic oligonucleotide, with long synthetic oligonucleotides, with a low level of misincorporated nucleotides, with chemicals or with enzymatic misincorporation of nucleotides also random mutagenesis PCR can be applied. For a detailed description see Ausubel et al., ibid. or Perbal, ibid. As an alternative to in vitro mutagenesis one can use in vivo mutagenesis either with the aid of UV-light or chemicals or by the application of an *E. coli* mutator strain (Fowler et al., J. Bacteriol., 1986, 167, 130).

Mutagenic nucleotides can be synthesised using apparatus obtainable from Applied Bio Systems.

4. Random mutanenesis by enzymatic misincorporation of nucleotides

A pMa/pMc gapped duplex can be subjected to primer extension and misincorporation mutagenesis as originally described by Shortle et al. (Proc. Natl. Acad. Sci. USA, 1982, 79, 1588) by B. C. Cunningham and J. A. Wells (Prot. Eng., 1987, 1, 319) a modification of this procedure is described by Lehtovaara et al., (Prot. Eng., 1988, 2, 63).

This method is based on controlled use of polymerases. Four populations of DNA molecules are first generated by primer elongation of a gapped duplex of pMa/pMc so that they terminate randomly, in the gap, but always just before a known type of base (before A, C, G or T, respectively). Each of four populations is then mutagenized in a separate misincorporation reaction where the correct base can now be omitted. In this way all types of base substitution mutations can be generated at every position of the gap. The use of sequenase (TM) (U.S. Biochemical Corporation) was preferred to the use of Klenow polymerase. Moreover MoMuLV reverse transcriptase was used instead of A.M.V. reverse transcriptase, which was used by Lehtovaara et al. (ibid).

To ensure single site substitutions we have introduced the following modification to the protocol described by Lehtovaara et al., ibid. In the reverse transcriptase buffer not three but only one misincorporating nucleotide is present. For instance the A-specific limited base elongation mixture is incubated in three separate reactions with 250 $\mu$M dCTP, 250 $\mu$M dGTP and 250 $\mu$M dTTP, respectively. For a complete set of 4 base specific limited elongation mixtures a total set of 12 separate misincorporation reactions is carried out. After 1.5 hour incubation at 42° C. a chase of all four deoxynucleotides in a concentration of 0.5 mM is added and the reactions are further incubated for at least 20 minutes at 37° C. Samples are then further processed according to Lehtovaara et al. (ibid.), with the modification that no counterselection to an uracil-containing DNA strand but a counterselection based on the pMa/c vector was applied.

5. Production of mutant α-amylases

Transformants of E. coli strain WK6 (Zell, R. and Fritz, H. J., EMBO J., 1987, 6, 1809), containing an expression vector, harboring any one of the α-amylase constructs, were inoculated in TB medium (10 ml) at 30° C. TB medium consisted of 0.017M KH$_2$PO$_4$, 0.072M K$_2$HPO$_4$, 12 g/l Bactotryptone, 24 g/l Bacto yeast extract, 0.4% glycerol and an antibiotic (ampicillin with pMa or chloramphenicol with pMc constructs). Samples of the culture were used to inoculate 250 ml TB in 2 liter flasks. At an OD$_{600}$ of 10–12, 0.1 mM IPTG (isopropyl-$\beta$-d-thiogalactopyranoside) was added and incubation continued for another 12–16 hours.

6. Purification of mutant α-amylases

The cells were harvested by centrifugation and resuspended in buffer containing 20% sucrose at 0° C. After a second centrifugation the cells were resuspended in cold water. Cell debris was removed by a third centrifugation and the supernatant was brought to pH 8.0 with 20 mM TRIS buffer. CaCl$_2$ was added to a final concentration of 50 mM. The material was heat-treated for 15 min. at 70° C. and the insoluble material removed by centrifugation. The supernatant was filtered through 0.22 $\mu$Millipore filter and concentrated to 1/10th of the starting volume.

Further purification was achieved using gelfiltration (on TSK HW-55- Merck) and Mono Q chromatography. Before chromatography on Mono S the pH, of the enzymatic activity containing fractions, was adjusted to 4.8 using sodium acetate. α-amylase was eluted with 250 mM NaCl. To avoid inactivation the pH was immediately adjusted to 8.0.

EXAMPLES

Example 1

Molecular cloning of Bacillus licheniformis α-amylase gene

Chromosomal DNA isolated from Bacillus licheniformis T5 (EP-A-134048; CBS 470.83) was digested with restriction enzyme EcoRI and ligated into the EcoRI site of pUB110 (Gryczan, T. J., et al., J. Bacteriol, 1978, 134., p 318). The ligation mixture was transformed into Bacillus subtilis 1A40 (Bacillus Genetic Stock Center). Neomycine resistant colonies were tested for α-amylase production on HI agar plates (DIFCO) supplemented with 0.4 g/l starch (Zulkowsky starch, Merck). After growth and incubation with I$_2$ vapor, a positive colony producing a large clearing halo was selected for further characterization. The plasmid isolated from this positive colony was shown to contain a 3.4 kb EcoRI-EcoRI fragment originating from Bacillus licheniformis T5. This plasmid was named pGB33 (EP-A-134048; CBS 466.83). The α-amylase encoding insert was ligated to a synthetic Shine-Dalgarno sequence and the bacteriophage SPO2 promoter resulting in plasmid pProm SPO$_2$ (see EP-A-0224294; CBS 696.85). The nucleotide sequence of the insert of pProm SPO$_2$ as determined by the method of Sanger (Proc. Natl. Acad. Sci. U.S.A., 1977, 74, 6463) is shown in FIG. 2. The sequence shows a single large open reading frame encoding an α-amylase (SEQ ID NO: 3), which is virtually identical to the α-amylase sequence of Bacillus licheniformis as determined by Yuuki et al. (ibid). The first 29 amino acids are a signal sequence which is cleaved off during secretion of the α-amylase. Numbering of amino acids throughout this application refers to the numbering according to the mature protein.

The Yuuki sequence differs at the following positions: at position 134 an Arg is present instead of Leu; at position 310 a Ser is present instead of Gly; at position 320 an Ala is present instead of Ser.

Example 2

Construction of mutagenesis/expression vectors pMaTLia6

Plasmid pPROM SPO$_2$ was digested with EcoRI and BclI and the 1.8 kb EcoRI-BclI insert was purified and cloned into EcoRI-BamHI digested pMa5-8. This pMa-5-8 vector was beforehand provided with a modified multiple cloning site. The BamHI-HindIII fragment running from position 3767 to position 3786 in FIG. 1 was exchanged for a synthetic DNA sequence as it reads from position 5647 to 5660 in FIG. 3. This was carried out to render some restriction sites within the α-amylase gene unique. The resulting α-amylase containing pMa5-8 derivative was digested with EcoRI and BamHI and ligated to a synthetic DNA fragment carrying a copy of the TAC promoter (De Boer et al., Proc. Natl. Acad. Sci. U.S.A., 1983, 80, 21). The sequence of this synthetic DNA fragment is depicted together with the final α-amylase mutagenesis/expression vector pMaTLia6 (SEQ ID NO: 4) in FIG. 3 from position 3757 to position 3859. This final α-amylase mutagenesis/expression vector was completed by the introduction of several silent restriction sites which are intended to produce gaps in the α-amylase gene during mutagenesis experiments (FIG. 4). For this purpose the following mutations have been made using site-directed oligonucleotide mutagenesis:

a SpeI site has been introduced by a silent mutation:

T 4 9 T     and     S 5 0 S
ACG ⟶ ACT         AGC ⟶ AGT a NarI site has been introduced by the silent mutation:

A2 6 9 A
GCG ⟶ GCC

A BstE II site has been introduced just downstream from the TAG stop codon
TAGAAGAGC→TAGGTGACC This α-amylase mutagenesis vector pMaTLia6 is suited for mutagenesis with the gapped duplex method. Double stranded pMaTLia6 DNA prepared by digestion of suitable restriction enzymes has been annealed to single stranded pMcTLia6 DNA.

The resulting single stranded gaps have been subjected to site-directed mutagenesis, to chemical mutagenesis and to random enzymatic mutagenesis as described in the experimental section.

The availability of the TAC promoter in front of the α-amylase gene enables the inducible expression of α-amylase in *E. coli* by addition of IPTG. Plasmid pMaTLia6 in *E. coli* WK6 was deposited as CBS 255.89 on Jun. 2nd, 1989.

Example 3

Construction of a Bacillus/*E. coli* shuttle vector for mutagenesis and expression This vector enables mutagenesis of an inserted gene in *E. coli* and immediate expression in Bacillus. The strategy chosen for the construction of the vector was to combine a pUB110 derivative (Gryczan, ibid.) with the pMa/c twin vector system in such a way that:
1. The *B. subtilis* cassette can be removed by a single restriction/religation experiment.
2. Different α-amylase genes and different promoters can be easily cloned in this vector.
3. After recircularisation the cloned gene will be under control of a suitable Bacillus promoter.
4. During mutagenesis in *E. coli* the Bacillus promoter and the structural α-amylase gene are physically separated preventing a possible lethal accumulation of α-amylase in *E. coli*.

A schematic drawing of the shuttle vector is shown in FIG. 5. The structure of the final version of the vector pBMa/cl is depicted in FIG. 6. Vector pBMa1 has been deposited under number CBS 252.89, on Jun. 2nd, 1989. The vector has been constructed as follows:

The EcoRI-SnaBI fragment of pUB110 carrying the REP-gene and the Neo ® gene was purified and cloned into EcoRI-SmaI digested pUC8.

The EcoRI-HindIII fragment of this pUC8 derivative was cloned into EcoRI-HindIII digested pMa5-8 resulting in plasmid pMa5-80.

The BamHI-XbaI polylinker fragment was substituted by a synthetic fragment of DNA encoding the SPO2 promoter of bacteriophage SPO2 (Williams et al., J. Bacteriol., 1981, 146, 1162) plus restriction recognition sites for SacII, ApaI, XhoI, SacI, BglII, MluI and XbaI.

The unique EcoRI site of pMa5-80 was used to insert a polylinker fragment constituting the following recognition sites: EcoRI, SmaI, SacI, EcoRV, SphI, KpnI, XbaI and HindIII For specific purposes derivatives pBMa/c2 and pBMa/c6 have been developed out of pBMa/cl.

In pBMa/c2 the EcoRI-HindIII polylinker of pBMa/cl has been replaced by the corresponding polylinker of pUC19.

In pBMa/c6 in addition the SacII site in the right polylinker of pBMa/cl has been removed by a Klenow reaction.

Site directed mutagenesis on the *B. licheniformis* α-amylase gene was performed after construction of pBMa/c6 Lia6. This vector was constructed by ligating the BamHI-HindIII fragment isolated from pMaTLia6 into the above mentioned pBMa/c6 which was cleaved by BamHI and HindIII. The resulting plasmid (FIG. 7) can be used to construct gapped duplexes for mutagenesis in *E. coli*.

The resulting mutants have been expressed in *Bacillus subtilis* 1A40 (BGSC 1A40) after restriction with SacI, religation and transformation according to Chang and Cohen (Mol. Gen. Genet., 1979, 168, 111).

Example 4

Expression in *E. coli* of correctly matured *Bacillus licheniformis* α-amylase

Characterization of the α-amylase produced by pMaTLia 6 (Example 2) showed that a portion of the α-amylase was incorrectly processed during secretion. $NH_2$-terminal sequencing revealed an extra Alanine residue for α-amylase produced in *E. coli* WK 6.

Although we have no indication that this will give different properties to the amylase we have replaced the α-amylase signal sequence by the alkaline phosphatase PhoA signal sequence. To this end a mutagenesis experiment was carried out so as to introduce a FspI restriction site in pMaTLia 6 at the junction of the signal peptide and the mature α-amylase. After FspI and BamHI digestion a synthetic DNA fragment encoding the phoA signal sequence (Michaelis et al. J. Bacteriol., 1983, 154, 366) was inserted. The sequence of this construction is shown in FIG. 8. α-Amylase produced by pMa/cTPLia6 was shown to possess the correct $NH_2$-terminal sequence.

Example 5

Screening for stable α-amylase

A. Screening for acid-stable α-amylase mutants

α-Amylase mutants, that perform better or worse at low pH than the wild-type α-amylase, can be selected by comparison of halo's on starch plates buffered at different pH values after staining the starch with an iodine-solution.

Method

1. Growth

Possible mutants are grown in microtiterplates. The growth medium is 250 μl Brain Heart Infusion broth (DIFCO). The following additions are made:

| | |
|---|---|
| chloramphenicol | 50 μg/ml |
| I.P.T.G. (SIGMA) | 0.2 mM |
| CaCl$_2$ | 2 mM |

Colonies are picked from agar plates with sterile toothpicks and inoculated in separate wells (96) of a microtiterplate. In each plate 4 wild-type colonies are included as a control.

These microtiterplates are placed at 37° C. for 40 hours without shaking.

2. Plate test

After this time period, in which the α-amylase is produced, 5 μl samples are taken from each well and spotted on 2 different types of agar plates (144×140 mm). The first type is a rich Heart-Infusion agar plate (DIFCO)+0.4% starch (Zulkowsky starch-Merck)+-chloramphenicol 50 μg/ml. After incubation at 37° C. for 16 hours this plate serves as a storage for mutants.

The second type of plate is the actual screening plate, it contains:

Bacto agar (DIFCO) 1.5%
Zulkowsky starch 0.2%

Agar and starch are dissolved in synthetic tap water (STW). This is: demineralised water +

| | |
|---|---|
| CaCl$_2$ | 2 mM |
| MgCl$_2$ | 1 mM |
| NaHCO$_3$ | 2.5 mM |
| BSA | 10 μg/ml |

The screening plates are buffered by a 100-fold dilution of a 5M stock potassium acetate buffer solution in this medium. pH values of the stock solutions are 4.80; 5.0 and 5.2 at room temperature. Final pH values in the agar plate when measured are somewhat lower than those of the stock solutions. From each well 5 μl of culture is spotted on 3 screening plates with different pH values.

The pH-range is chosen in such a way that there is little or no activity left for the wild-type α-amylase on the plate with the lowest pH-value.

3. Coloring

The screening plates are incubated for 2 hours at 55° C. After this period an I$_2$ solution is poured over the plates. 10×I$_2$ solution contains 30 g I$_2$ and 70 g KI per liter.

The amount of clearance of the spots is correlated with the residual α-amylase activity at that pH value. Those mutants that perform better than the wild-type controls are selected for a second round of screening. Wild-type halo's are very reproducible in this experiment.

4. Second screening

Positive mutants are picked from the rich plate and purified on fresh HI plates +chloramphenicol. 4 single colonies are picked from each mutant and they are tested again in a similar way as in the first screening. In addition serial dilutions of these cultures are made with STW and these dilutions are spotted on neutral pH screening plates (pH=7.0). Comparison with wild-type cultures enables one to decide if the better performance at low pH is due to an overall better α-amylase production or to intrinsically more stable α-amylase.

The mutants that "survive" the second screening are characterized by determining the nucleotide sequence of that part of the gene that was subjected to mutagenesis.

B. Screening for alkali stable α-amylase

Screening for alkali stable α-amylases is performed in a manner similar to the one used for acid stable α-amylase. After growth in microtiter plates 5 μl samples are taken from each well and spotted onto a storage plate and onto the actual screening plate. The latter is composed of:

| | |
|---|---|
| Bacto Agar (DIFCO) | 1.5% |
| Zulkowsky starch | 0.2% | and completed with demineralized water plus

| | |
|---|---|
| CaCl$_2$ | 2 mM |
| MgCl$_2$ | 1 mM |
| NaHCO$_3$ | 2.5 mM |
| BSA | 10 μg/ml |

The screening plates are buffered with 50 mM carbonate/bicarbonate buffer, pH values are 9.0, 9.5 and 10.0. The pH range is chosen in such a way that there is little or no activity of the wild-type α-amylase at the highest pH value. After 2 hours incubation at 55° C. an I$_2$ solution is poured over the plates. Those mutants that give a better halo than the wild-type enzyme are selected for a second round of screening. This second round of screening is performed in a similar fashion as the screening for the acid stability.

C. Screening for thermostable α-amylase mutants

α-Amylase mutants that perform better or worse at high temperature than the wild-type α-amylase, can also be selected by comparison of halo's on starch plates caused by the residual amylase activity in the culture broths after heating.

Method

1. Mutants are grown in the same way as for the pH-screening.
2. The mutants are replicated on HI agar plates as for the pH-screening.
3. The separate wells of the microtiterplates were closed with disposable caps (Flow laboratories) to prevent evaporation of the culture broths during the heating step.
4. Microtiterplates were heated in a waterbath for 1 hour at 95° C. After heating the microtiterplates were placed in a centrifuge for collecting the total sample on the bottom of the microtiterplate.
5. Screening for thermostable mutants was done as follows:

From each well 5 μl of culture was spotted on neutral screeningplates (See pH-screening). These plates were incubated for 1 hour at 55° C. After staining the starch with the iodine solution mutants and controls can be screened for residual α-amylase activity by comparing clearance of the spots (halo's).

In case the residual activity of the controls is too high, serial dilutions must be made and spotted on the screening plate to be able to discriminate for mutants that are more thermostable than the wild-type enzyme.

6. Possible interesting mutants are tested further as was done in the pH-screening method.

A combination of screening type A or B with type C can be applied if a combination of properties is desired. For instance after the first round of screening for alkali stable α-amylase, a second round of screening for thermostability can be performed. Those mutants that score positive in both tests may be selected as candidates exhibiting a combination of desired properties.

Example 6

Bisulphite mutagenesis of pMaTLia6

Single stranded DNA of pMaTLia6 was annealed with SacII-ClaI digested pMcTLia6 in order to obtain a heteroduplex with a gap running from position 4315 to 4569 (FIG. 3). This heteroduplex was subjected to bisulphite mutagenesis (see experimental).

After transformation into *E. coli* WK6 mut S (Zell, R. and Fritz H. J., ibid) and selection on chloramphenicol containing agar plates (50 μg/ml) plasmid pools were isolated and transformed into *E. coli* WK6. *E. coli* WK6 Mut S was deposited as CBS 472.88, *E. coli* WK6 was deposited as CBS 473.88. Resulting transformants were grown in BHI medium (DIFCO) containing 2.0 mM CaCl2, 50 μg/ml chloramphenicol and 0.20 mM IPTG (SIGMA) during 40 hours at 37° C. in microtiter wells without shaking. Screening for pH stable mutants was carried out as described in Example 5.

About 300 Cm ® transformants were screened. The mutation frequency as determined by DNA sequencing was on average 0.4 mutation/molecule over the gap. One acid stable mutant, D7, was identified after the pH screening. Sequencing of this mutant revealed mutation H133Y originating from a mutation of the encoding triplet from CAC to TAC.

Mutant D7 was also found positive in the thermo-stability screening assay (Example 5).

DNA sequencing was performed on single stranded DNA with a specific oligonucleotide designed to prime just before the SacII-ClaI fragment. In a separate mutagenesis experiment 1000 Cm ® transformants were screened. Another acid stable mutant, 2D5, was identified after the pH screening. This mutant has the following mutations:

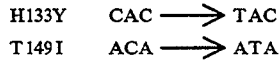

Bisulphite mutagenesis has been applied in a similar manner as just described on the ClaI-SalI gap which runs from position 4569 to position 4976 of FIG. 3. About 300 Cm ® transformants were screened (mutation frequency 0.6 mutations/molecule). No acid stable transformants were found. A number of acid labile mutants were found. Among these acid labile mutants some may have a shifted pH spectrum resulting in a more alkaline stable phenotype.

Example 7

Enzymatic mutagenesis of pMaTLia6

Single stranded pMaTLia6 (FIG. 4) was annealed with ClaI-SalI digested pMcTLia6 in order to obtain a heteroduplex running from position 4569 to 4976 (FIG. 3). The gapped duplex was subjected to enzymatic misincorporation mutagenesis as described in the experimental section.

A sample obtained after dATP-limited primer elongation was split in three parts and incubated in the presence of reverse transcriptase with dCTP, dGTP and dTTP, respectively. After incubation at 37° C. for 10 minutes a chase with all four dNTP's and Klenow polymerase was given T4-DNA ligase was added to finish the elongation to completely double stranded molecules.

These molecules were transformed into *E. coli* WK 6 Mut S and plasmid pools were recovered. These plasmid pools were subsequently transformed into . *E. coli* WK 6 and the colonies were selected on chloramphenicol (50 μg/ml) containing agar plates. Resulting mutants were screened for stability of α-amylase as described in Example 5.

In another experiment the SpeI-SacII gap was subjected to limited primer elongation with dATP, dCTP, dGTP and dTTP, respectively. These primer pools were mutagenized by misincorporation (see experimental). 100 Cm ® transformants were tested on pH plates (Example 5) and mutant M29 was identified as more stable at low pH. The sequence of the mutation was determined: A111T GCG→TCG

Example 8

Properties of stable mutants

Two of the mutants obtained from the bisulphite mutagenesis experiments were further characterized. As described before DNA sequencing suggested the following amino acid replacements;

D7 contained a tyrosine at position 133 instead of a histidine (D7=H133Y),

2D5 contained the D7 mutation and in addition threonine 149 was replaced by isoleucine (2D5=H133Y, T149I).

a) Measurement of enzymatic activity

The enzymatic activity of *B. licheniformis* α-amylase WT and mutants was measured using 4-nitrophenyl-maltopentaoside (4NP-DP5) as a substrate, 4 nitrophenol and maltopentaose are formed, this reaction can be followed by measuring the change in OD 405 The assay was performed at 35° C. in 50 mM MOPS, 50 mM NaCl, 2 mM CaCl2 (PH 7.15) and 0-1 mM 4NP-DP5.

Initial rates were measured and E-nitrophenol was taken as 10,000 l/M/cm. FIG. 9 shows the results for WT and 2D5 α-amylases. Vmax and Km were calculated and are given in Table 1.

TABLE 1

|  | Vmax (μmol/min/mg) | Km (mM) |
|---|---|---|
| WT | 66.7 ± 0.9 | 0.112 ± 0.005 |
| 2D5 | 66.3 ± 0.7 | 0.119 ± 0.004 |

Table 1 clearly shows that the mutations of α-amylase 2D5 do not influence the enzymatic activity in a substantial way.

b) Influence of Ca²⁺ on the thermoinactivation

Heat inactivation experiments were performed for WT, D7 and 2D5 at varying calcium concentrations. The procedure was as follows:

1) Demetallization

Enzyme (2-3 mg/ml) dialyzed for 24 hrs against

| 3 × 1 L | 20 mM MOPS |
|---|---|
|  | 5 mM EDTA |
|  | 5 mM EGTA pH 7.0 |
| 3 × 1 L | 20 mM MOPS pH 7.0 |

2) Remetallization

500 μl buffer 100 mM (e.g. MES, MOPS, EPPS)*
145 μl demetallized enzyme (e.g. 2.15 mg/ml)
100 μl CaCl$_2$ (100, 50, 30, 20, 10, 5 or 2.5 mM)
x μl K$_2$SO$_4$ (100 mM)
(255-x) μl H$_2$O

| [CaCl$_2$] final (mM) | [K$_2$SO$_4$] final (mM) |
| --- | --- |
| 0,25 | 14,75 |
| 0,5 | 14,5 |
| 1 | 14 |
| 2 | 13 |
| 3 | 12 |
| 5 | 10 |
| 10 | 0 | pH MES e.g. 6.77 at room temperature will give 6.0 at 90° C. (pKa 6.15 pKa/° C.=−0.011)
pKa were from Table of Merck (Zwitterionische Puffersubstanzen)

3) Heat-inactivation 1 ml enzyme solution preincubated at room temperature was heated at 90.5° C. or 95° C. in closed Pierce-vials (teflon coated-seals) at a concentration of about 0.2 mg/ml. 50 μl samples were withdrawn at regular intervals between 0 and 6 hrs with a syringe and cooled on ice. Residual activities have been determined with 4NP-DP5 (0.5 mM).

Half lives were determined using a single exponential decay fitting program (GRAPHPAD).

FIGS. 10 and 11 show the half life times of WT and D7 α-amylases at pH 5.5 and 7.0 respectively as a function of the Ca$^{2+}$ concentration at 90.5° C. The Ca$^{2+}$ dependence of 2D5 has only been determined at pH 7.0 at 95° C. (FIG. 12). It can also be seen that the Ca$^{2+}$ dependence of the mutants is not different from that of the WT.

c. Thermostability of mutant α-amylases at different pH values

The pH dependence of thermoinactivation for both D7 and 2D5 has been determined at 90.5° and 95° C. respectively using the buffer as described above at a 1 mM Ca$^{2+}$ concentration. It can be concluded that the thermal stability of both D7 and 2D5 is greatly increased (up to twofold for 2D5) over the entire pH range. (FIGS. 13 and 14).

Example 9

Production of mutant enzymes in Bacillus

Mutations in the B. licheniformis α-amylase, which were identified by expression in E. coli WK6 were transferred to a Bacillus expression vector in two different ways.

a) With the aid of the unique restriction sites within the α-amylase gene (FIG. 4), fragments carrying mutations were isolated from pMaTLia6 mutants and subcloned into the homologous position of pBMa6.Lia6. The latter plasmid, which can be replicated either in E. coli or in Bacillus, was subsequently digested with SacI and recircularized with T4 DNA ligase. After transformation into Bacillus subtilis 1A40 high level α-amylase production under control of the SPO$_2$ promoter was obtained. Recircularized pBMa6.Lia6 is named pB6.Lia6 to indicate the removal of the E. coli portion of the vector.

b) pBMa6.Lia6 single stranded DNA was recollected from E. coli and annealed with restriction enzyme digested pBMc6.Lia6 double stranded DNA in order to obtain a gapped duplex with the intended gap on the α-amylase gene. This gap was then subjected to site-directed mutagenesis with an oligonucleotide (as described in the experimental section) which encodes the desired mutation. pBMc6.Lia6 vector is then transformed into pB6.Lia6 type vector as described above. Combination of different single site mutation can be performed by method a) if mutations are in different gaps, preferably, however, method b) is used.

The mutations of mutants D7 and 2D5 were transferred to pBMa6.Lia6 by method a) by exchanging the SacII-SalI fragments and α-amylase was recovered from the medium of transformed Bacillus subtilis 1A40. Supernatants of both mutants were subjected to the screening procedures of Examples and it was confirmed that both mutants produce α-amylase which is more acid stable and more thermostable than α-amylase produced by wild-type pB6.Lia6.

The phenotype of the α-amylase mutations in Bacillus is thus not different from the phenotype in E. coli.

Ultimately pB6.Lia6 mutants have been transformed into Bacillus licheniformis T9, which is a protease negative, α-amylase negative derivative of Bacillus licheniformis T5, (EP-0253455, CBS 470.83). Host T9 has been used to produce high level amounts of α-amylase mutants in a homologous system. The removal of the chromosomal α-amylase gene renders this strain very suited for the production of mutant α-amylase as no contaminating wild-type α-amylase is being produced anymore. Enzyme recovered from this strain has been used for industrial application testing. The industrial use of mutants pB6.Lia6.2D5 and pB6.Lia6.D7 was demonstrated.

Example 10

Application test of mutant α-amylase under conditions of starch liquefaction

To test mutant α-amylase 2D5 in more realistic circumstances, we have purified the fermentation broth (of Example 9) with ultrafiltration and formulated the enzyme with 50% propyleneglycol.

Three samples have been tested:

| 893701: WT | B. licheniformis T5 α-amylase | 1530 TAU/G |
| 893703: 2D5 | Mutant prepared as WT | 2820 TAU/G |
| Maxamyl 0819 | Commercial sample | 7090 TAU/G |

One TAU (thermostable α-amylase unit) is defined as the quantity of enzyme that will convert under standardized conditions 1 mg of starch per minute in a product having an equal absorption to a reference colour at 620 nm after reaction with iodine. Standard conditions are pH 6.6; 30° C.; reaction time: 20 min. Reference colour is 25 g CoCl$_2$. 6H$_2$O, 3.84 g K$_2$Cr$_2$O$_7$ and 1 ml HCl (1M) in 100 ml destilled H$_2$O.

1. Liquefaction test at low pH (5.5 and 5.25)

The temperature of starch slurry is increased to 110°±0.5° C. as quick as possible and kept at this temperature for 6 minutes.

The liquefaction is realized in continuous flow (5.4 l/h). 3 Samples of 135 ml (1.5 minute of liquefaction) are taken after 45, 60 and 75 minutes of liquefaction and kept at 95° C. for two hours. After this time, 50 ml of the sample are acidified with 0.4 ml H$_2$SO$_4$ N to obtain pH 3.5 and put in boiling bath for 10 minutes in order to stop enzymatic activity before D.E. determination.

The remaining part of the sample is cooled in order to determine residual enzymatic activity.

Slurry composition:
3.3 kg corn starch D.S. 88% (2,904 kg dry starch).
5.45 l well water (40 T.H.).
Dry substance of the slurry is 33%.
pH is corrected at 5.5 with 1N sulfuric acid or 1N NaOH.
Enzyme concentration:
4.4 TAU/gr dry starch.

The flow rate is verified two or three times during the trial.

2. Determination of D.E.

Dry substance of liquefied starch is verified with a refractometer (about 34%). D.E. is determined with the well-known Lane Eynon method. The results are shown in FIG. 15.

3. Residual Enzymatic Activity

Residual amylase activity in liquefied starch is determined with a Brabender amylograph.
40 g potato starch
390 ml distilled water at 50° C.
50 ml Tris buffer 0.05 M pH 6.50
5 ml CaCl$_2$ 2H$_2$O at 30 g/l The temperature is increased to 80° C. (1.5°/min) when viscosity is stabilized (10 min) 5 ml of diluted liquefied starch (7 g up to 50 ml with distilled water) is added, the decrease of viscosity after 20 minutes is measured, this decrease is a function of the enzymatic activity. A standard curve with known enzymatic concentration allows to estimate residual activity in T.A.U.

Mutant 2D5 performs significantly better at pH<5.5° and 110° C. than WT enzyme. An improvement of 2-3 DE units at pH 5.25 is obtained with mutant 2D5.

Example 11

Application test of mutant α-amylase under conditions of textile desizing

To test the industrial application of alkaline α-amylase mutants a test is performed on the stability at 20° C. in the following solution:

| | |
|---|---|
| 1.4% | H$_2$O$_2$ (35%) |
| 1.0–1.5% | Caustic Soda (100%) |
| 15–20 ml/l | Sodium Silicate (38 Be) |
| 0.3–0.5% | Alkylbenzene sulphonate (Lanaryl N.A.-ICI) |
| 0.5–1.0% | Organic stabilizer (Tinoclarite G) |

After incubation during 2.5 hours the α-amylase mutants selected for their desired properties should have any remaining enzyme activity.

We claim:

1. An isolated mutant α-amylase wherein said mutant α-amylase has a replacement of at least one amino acid in a corresponding wild-type α-amylase obtainable from *Bacillus licheniformis* and wherein said mutant α-amylase exhibits one or more improved properties relative to the wild-type α-amylase selected from the group consisting of improved thermostability, improved stability at a pH below 6.5, improved stability at a pH above 7.5, and improved acid stability as a result of said replacement, wherein said replacement is one or more amino acid replacements selected from the group consisting of Ala-111-Thr, His-133-Tyr and Thr-149-Ile.

2. A DNA encoding the mutant α-amylase claim 1.

3. An expression vector which comprises a DNA according to claim 2.

4. A host cell containing an expression vector according to claim 3.

5. A method for the degradation of starch which comprises:
   contacting said starch with a mutated α-amylase according claim 1 for a sufficient time and under conditions whereby said α-amylase degrades said starch.

6. A method for textile desizing which comprises:
   contacting sized textile with a mutated α-amylase according claim 1 for a sufficient time and under conditions whereby said sized textile is desized.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 3803 base pairs
        ( B ) TYPE: nucleic acid
        ( C ) STRANDEDNESS: double
        ( D ) TOPOLOGY: circular ( x i ) SEQUENCE DESCRIPTION: SEQ ID NO:1:

```
AATTCACCTC  GAAAGCAAGC  TGATAAACCG  ATACAATTAA  AGGCTCCTTT  TGGAGCCTTT    60
TTTTTGGAG   ATTTTCAACG  TGAAAAAATT  ATTATTCGCA  ATTCCAAGCT  AATTCACCTC   120
GAAAGCAAGC  TGATAAACCG  ATACAATTAA  AGGCTCCTTT  TGGAGCCTTT  TTTTTGGAG    180
ATTTTCAACG  TGAAAAAATT  ATTATTCGCA  ATTCCAAGCT  CTGCCTCGCG  CGTTTCGGTG   240
ATGACGGTGA  AAACCTCTGA  CACATGCAGC  TCCCGGAGAC  GGTCACAGCT  TGTCTGTAAG   300
CGGATGCAGA  TCACGCGCCC  TGTAGCGGCG  CATTAAGCGC  GGCGGGTGTG  GTGGTTACGC   360
GCAGCGTGAC  CGCTACACTT  GCCAGCGCCC  TAGCGCCCGC  TCCTTTCGCT  TTCTTCCCTT   420
CCTTTCTCGC  CACGTTCGCC  GGCTTTCCCC  GTCAAGCTCT  AAATCGGGGG  CTCCCTTTAG   480
GGTTCCGATT  TAGTGCTTTA  CGGCACCTCG  ACCCCAAAAA  ACTTGATTAG  GGTGATGGTT   540
CACGTAGTGG  GCCATCGCCC  TGATAGACGG  TTTTTCGCCC  TTTGACGTTG  GAGTCCACGT   600
TCTTTAATAG  TGGACTCTTG  TTCCAAACTG  GAACAACACT  CAACCCTATC  TCGGTCTATT   660
CTTTTGATTT  ATAAGGGATT  TTGCCGATTT  CGGCCTATTG  GTTAAAAAAT  GAGCTGATTT   720
AACAAAAATT  TAACGCGAAT  TTTAACAAAA  TATTAACGTT  TACAATTTGA  TCTGCGCTCG   780
GTCGTTCGGC  TGCGGCGAGC  GGTATCAGCT  CACTCAAAGG  CGGTAATACG  GTTATCCACA   840
GAATCAGGGG  ATAACGCAGG  AAAGAACATG  TGAGCAAAAG  GCCAGCAAAA  GGCCAGGAAC   900
```

```
CGTAAAAAGG CCGCGTTGCT GGCGTTTTTC CATAGGCTCC GCCCCCCTGA CGAGCATCAC  960
AAAAATCGAC GCTCAAGTCA GAGGTGGCGA AACCCGACAG GACTATAAAG ATACCAGGCG 1020
TTTCCCCCTG GAAGCTCCCT CGTGCGCTCT CCTGTTCCGA CCCTGCCGCT TACCGGATAC 1080
CTGTCCGCCT TTCTCCCTTC GGGAAGCGTG GCGCTTTCTC AATGCTCACG CTGTAGGTAT 1140
CTCAGTTCGG TGTAGGTCGT TCGCTCCAAG CTGGGCTGTG TGCACGAACC CCCCGTTCAG 1200
CCCGACCGCT GCGCCTTATC CGGTAACTAT CGTCTTGAGT CCAACCCGGT AAGACACGAC 1260
TTATCGCCAC TGGCAGCAGC CACTGGTAAC AGGATTAGCA GAGCGAGGTA TGTAGGCGGT 1320
GCTACAGAGT TCTTGAAGTG GTGGCCTAAC TACGGCTACA CTAGAAGGAC AGTATTTGGT 1380
ATCTGCGCTC TGCTGAAGCC AGTTACCTTC GGAAAAAGAG TTGGTAGCTC TTGATCCGGC 1440
AAACAAACCA CCGCTGGTAG CGGTGGTTTT TTTGTTTGCA AGCAGCAGAT TACGCGCAGA 1500
AAAAAAGGAT CTCAAGAAGA TCCTTTGATC TTTTCTACGG GGTCTGACGC TCAGTGGAAC 1560
GAAAACTCAC GTTAAGGGAT TTTGGTCATG AGATTATCAA AAAGGATCTT CACCTAGATC 1620
CTTTTAAATT AAAAATGAAG TTTTAAATCA ATCTAAAGTA TATATGAGTA AACTTGGTCT 1680
GACAGTTACC AATGCTTAAT CAGTGAGGCA CCTATCTCAG CGATCTGTCT ATTTCGTTCA 1740
TCCATAGTTG CCTGACTCCC CGTCGTGTAG ATAACTACGA TACGGGAGGG CTTACCATCT 1800
GGCCCCAGTG CTGCAATGAT ACCGCGAGAC CCACGCTCAC CGGCTCCAGA TTTATCAGCA 1860
ATAAACCAGC CAGCCGGAAG GGCCGAGCGC AGAAGTGGTC CTGCAACTTT ATCCGCCTCC 1920
ATCCAGTCTA TTAATTGTTG CCGGGAAGCT AGAGTAAGTA GTTCGCCAGT TAATAGTTTG 1980
CGCAACGTTG TTGCCATTGC TGCAGGCATC GTGGTGTCAC GCTCGTCGTT TGGTATGGCT 2040
TCATTCAGCT CCGGTTCCCA ACGATCAAGG CGAGTTACAT GATCCCCCAT GTTGTGCAAA 2100
AAAGCGGTTA GCTCCTTCGG TCCTCCGATC GTTGTCAGAA GTAAGTTGGC CGCAGTGTTA 2160
TCACTCATGG TTATGGCAGC ACTGCATAAT TCTCTTACTG TCATGCCATC CGTAAGATGC 2220
TTTTCTGTGA CTGGTGAGTA CTCAACCAAG TCATTCTGAG AATAGTGTAT GCGGCGACCG 2280
AGTTGCTCTT GCCCGGCGTC AACACGGGAT AATACCGCGC CACATAGCAG AACTTTAAAA 2340
GTGCTCATCA TTGGAAAACG TTCTTCGGGG CGAAAACTCT CAAGGATCTT ACCGCTGTTG 2400
AGATCCAGTT CGATGTAACC CACTCGTGCA CCCAACTGAT CTTCAGCATC TTTTACTTTC 2460
ACCAGCGTTT CTGGGTGAGC AAAAACAGGA AGGCAAAATG CCGCAAAAAA GGGAATAAGG 2520
GCGACACGGA AATGTTGAAT ACTCATACTC TTCCTTTTTC AATATTATTG AAGCAGACAG 2580
TTTTATTGTT CATGATGATA TATTTTTATC TTGTGCAATG TAACATCAGA GATTTTGAGA 2640
CACAACGTGG CTTTGTTGAA TAAATCGAAC TTTTGCTGAG TTGACTCCCC GCGCGCGATG 2700
GGTCGAATTT GCTTTCGAAA AAAAGCCCG CTCATTAGGC GGGCTAAAAA AAGCCCGCT 2760
CATTAGGCGG GCTCGAATTT CTGCCATTCA TCCGCTTATT ATCACTTATT CAGGCGTAGC 2820
AACCAGGCGT TTAAGGGCAC CAATAACTGC CTTAAAAAAA TTACGCCCCG CCCTGCCACT 2880
CATCGCAGTA CTGTTGTAAT TCATTAAGCA TTCTGCCGAC ATGGAAGCCA TCACAGACGG 2940
CATGATGAAC CTGAATCGCC AGCGGCATCA GCACCTTGTC GCCTTGCGTA TAATATTTGC 3000
CCATAGTGAA AACGGGGGCG AAGAAGTTGT CCATATTCGC CACGTTTAAA TCAAAACTGG 3060
TGAAACTCAC CCAGGGATTG GCTGAGACGA AAAACATATT CTCAATAAAC CCTTTAGGGA 3120
AATAGGCCAG GTTTTCACCG TAACACGCCA CATCTTGCGA ATATATGTGT AGAAACTGCC 3180
GGAAATCGTC GTGGTATTCA CTCCAGAGCG ATGAAAACGT TTCAGTTTGC TCATGGAAAA 3240
CGGTGTAACA AGGGTGAACA CTATCCCATA TCACCAGCTC ACCGTCTTTC ATTGCCATAC 3300
GAAATTCCGG ATGAGCATTC ATCAGGCGGG CAAGAATGTG AATAAAGGCC GGATAAAACT 3360
```

-continued

```
TGTGCTTATT TTTCTTTACG GTCTTTAAAA AGGCCGTAAT ATCCAGCTAA ACGGTCTGGT    3420
TATAGGTACA TTGAGCAACT GACTGAAATG CCTCAAAATG TTCTTTACGA TGCCATTGGG    3480
ATATATCAAC GGTGGTATAT CCAGTGATTT TTTTCTCCAT TTTAGCTTCC TTAGCTCCTG    3540
AAAATCTCGA TAACTCAAAA AATACGCCCG GTAGTGATCT TATTTCATTA TGGTGAAAGT    3600
TGGAACCTCT TACGTGCCGA TCAACGTCTC ATTTTCGCCA AAAGTTGGCC CAGGGCTTCC    3660
CGGTATCAAC AGGGACACCA GGATTTATTT ATTCTGCGAA GTGATCTTCC GTCACAGGTA    3720
TTTATTCGAA GACGAAAGGG CATCGCGCGC GGGGAATTCC CGGGGATCCG TCGACCTGCA    3780
GCCAAGCTTG GTCTAGAGGT CGA                                            3803
```

(2) INFORMATION FOR SEQ ID NO:2:

(i) SEQUENCE CHARACTERISTICS:
    (A) LENGTH: 2149 base pairs
    (B) TYPE: nucleic acid
    (C) STRANDEDNESS: double
    (D) TOPOLOGY: linear (ix) FEATURE:
    (A) NAME/KEY: CDS
    (B) LOCATION: 382..1920

(ix) FEATURE:
    (A) NAME/KEY: matpeptide
    (B) LOCATION: 469..1920

(xi) SEQUENCE DESCRIPTION: SEQ ID NO:2:

```
GTCTACAAAC CCCTTAAAAA CGTTTTTAAA GGCTTTTAAG CCGTCTGTAC GTTCCTTAAG     60
GAATTCACAC TGGCCTTGGT TAAGGTTAAG ATGTGGACGG AATGGGTAAA GTGTAGTAAA    120
GTACAATTAA TCGGGAGCTT AGATGTCCCT TCAACATCTT ATATAGAAGG GAAGGTTGGC    180
AAATGGAAAT TGAAAGAATT AACGAGCATA CAGTAAAATT TTATATGTCT TACGGAGATA    240
TTGAAGATCG CGGTTTTGAC AGAGAAGAAA TTTGGTATAA CCGTGAGCGC AGTGAAGAAC    300
TTTTCTGGGA AGTCATGGAT GAAGTTCATG AAGAAGAGGA ATTCGAGCTC GCCCGGGGAT    360
CCAAGGAGGT GATCTAGAGT C ATG AAA CAA CAA AAA CGG CTT TAC GCC CGA     411
                        Met Lys Gln Gln Lys Arg Leu Tyr Ala Arg
                        -29              -25                  -20

TCT GTG ACG CTG TTA TTT GCG CTC ATC TTC TTG CTG CCT CAT TCT GCA     459
Ser Val Thr Leu Leu Phe Ala Leu Ile Phe Leu Leu Pro His Ser Ala
            -15                 -10                  -5

GCA GCG GCG GCA AAT CTT AAT GGG ACG CTG ATG CAG TAT TTT GAA TGG     507
Ala Ala Ala Ala Asn Leu Asn Gly Thr Leu Met Gln Tyr Phe Glu Trp
             1               5                      10

TAC ATG CCC AAT GAC GGC CAA CAT TGG AAG CGT TTG CAA AAC GAC TCG     555
Tyr Met Pro Asn Asp Gly Gln His Trp Lys Arg Leu Gln Asn Asp Ser
         15                  20                  25

GCA TAT TTG GCT GAA CAC GGT ATT ACT GCC GTC TGG ATT CCC CCG GCA     603
Ala Tyr Leu Ala Glu His Gly Ile Thr Ala Val Trp Ile Pro Pro Ala
 30                  35                  40                  45

TAT AAG GGA ACG AGC CAA GCG GAT GTG GGC TAC GGT GCT TAC GAC CTT     651
Tyr Lys Gly Thr Ser Gln Ala Asp Val Gly Tyr Gly Ala Tyr Asp Leu
                 50                  55                  60

TAT GAT TTA GGG GAG TTT CAT CAA AAA GGG ACG GTT CGG ACA AAG TAC     699
Tyr Asp Leu Gly Glu Phe His Gln Lys Gly Thr Val Arg Thr Lys Tyr
             65                  70                  75

GGC ACA AAA GGA GAG CTG CAA TCT GCG ATC AAA AGT CTT CAT TCC CGC     747
Gly Thr Lys Gly Glu Leu Gln Ser Ala Ile Lys Ser Leu His Ser Arg
         80                  85                  90

GAC ATT AAC GTT TAC GGG GAT GTG GTC ATC AAC CAC AAA GGC GGC GCT     795
Asp Ile Asn Val Tyr Gly Asp Val Val Ile Asn His Lys Gly Gly Ala
```

-continued

|  |  |  | 95 |  |  |  | 100 |  |  |  | 105 |  |  |  |  |
|---|---|---|---|---|---|---|---|---|---|---|---|---|---|---|---|
| GAT | GCG | ACC | GAA | GAT | GTA | ACC | GCG | GTT | GAA | GTC | GAT | CCC | GCT | GAC | CGC | 843
| Asp | Ala | Thr | Glu | Asp | Val | Thr | Ala | Val | Glu | Val | Asp | Pro | Ala | Asp | Arg |
| 110 |  |  |  |  | 115 |  |  |  |  | 120 |  |  |  |  | 125 |

| AAC | CGC | GTA | ATT | TCA | GGA | GAA | CAC | CTA | ATT | AAA | GCC | TGG | ACA | CAT | TTT | 891
| Asn | Arg | Val | Ile | Ser | Gly | Glu | His | Leu | Ile | Lys | Ala | Trp | Thr | His | Phe |
|  |  |  |  | 130 |  |  |  |  | 135 |  |  |  |  | 140 |  |

| CAT | TTT | CCG | GGG | CGC | GGC | AGC | ACA | TAC | AGC | GAT | TTT | AAA | TGG | CAT | TGG | 939
| His | Phe | Pro | Gly | Arg | Gly | Ser | Thr | Tyr | Ser | Asp | Phe | Lys | Trp | His | Trp |
|  |  |  | 145 |  |  |  |  | 150 |  |  |  |  | 155 |  |  |

| TAC | CAT | TTT | GAC | GGA | ACC | GAT | TGG | GAC | GAG | TCC | CGA | AAG | CTG | AAC | CGC | 987
| Tyr | His | Phe | Asp | Gly | Thr | Asp | Trp | Asp | Glu | Ser | Arg | Lys | Leu | Asn | Arg |
|  |  | 160 |  |  |  |  | 165 |  |  |  |  | 170 |  |  |  |

| ATC | TAT | AAG | TTT | CAA | GGA | AAG | GCT | TGG | GAT | TGG | GAA | GTT | TCC | AAT | GAA | 1035
| Ile | Tyr | Lys | Phe | Gln | Gly | Lys | Ala | Trp | Asp | Trp | Glu | Val | Ser | Asn | Glu |
|  | 175 |  |  |  |  | 180 |  |  |  |  | 185 |  |  |  |  |

| AAC | GGC | AAC | TAT | GAT | TAT | TTG | ATG | TAT | GCC | GAC | ATC | GAT | TAT | GAC | CAT | 1083
| Asn | Gly | Asn | Tyr | Asp | Tyr | Leu | Met | Tyr | Ala | Asp | Ile | Asp | Tyr | Asp | His |
| 190 |  |  |  |  | 195 |  |  |  |  | 200 |  |  |  |  | 205 |

| CCT | GAT | GTC | GCA | GCA | GAA | ATT | AAG | AGA | TGG | GGC | ACT | TGG | TAT | GCC | AAT | 1131
| Pro | Asp | Val | Ala | Ala | Glu | Ile | Lys | Arg | Trp | Gly | Thr | Trp | Tyr | Ala | Asn |
|  |  |  | 210 |  |  |  |  | 215 |  |  |  |  | 220 |  |  |

| GAA | CTG | CAA | TTG | GAC | GGT | TTC | CGT | CTT | GAT | GCT | GTC | AAA | CAC | ATT | AAA | 1179
| Glu | Leu | Gln | Leu | Asp | Gly | Phe | Arg | Leu | Asp | Ala | Val | Lys | His | Ile | Lys |
|  |  |  |  | 225 |  |  |  |  | 230 |  |  |  |  | 235 |  |

| TTT | TCT | TTT | TTG | CGG | GAT | TGG | GTT | AAT | CAT | GTC | AGG | GAA | AAA | ACG | GGG | 1227
| Phe | Ser | Phe | Leu | Arg | Asp | Trp | Val | Asn | His | Val | Arg | Glu | Lys | Thr | Gly |
|  |  | 240 |  |  |  |  | 245 |  |  |  |  | 250 |  |  |  |

| AAG | GAA | ATG | TTT | ACG | GTA | GCT | GAA | TAT | TGG | CAG | AAT | GAC | TTG | GGC | GCG | 1275
| Lys | Glu | Met | Phe | Thr | Val | Ala | Glu | Tyr | Trp | Gln | Asn | Asp | Leu | Gly | Ala |
|  | 255 |  |  |  |  | 260 |  |  |  |  | 265 |  |  |  |  |

| CTG | GAA | AAC | TAT | TTG | AAC | AAA | ACA | AAT | TTT | AAT | CAT | TCA | GTG | TTT | GAC | 1323
| Leu | Glu | Asn | Tyr | Leu | Asn | Lys | Thr | Asn | Phe | Asn | His | Ser | Val | Phe | Asp |
| 270 |  |  |  |  | 275 |  |  |  |  | 280 |  |  |  |  | 285 |

| GTG | CCG | CTT | CAT | TAT | CAG | TTC | CAT | GCT | GCA | TCG | ACA | CAG | GGA | GGC | GGC | 1371
| Val | Pro | Leu | His | Tyr | Gln | Phe | His | Ala | Ala | Ser | Thr | Gln | Gly | Gly | Gly |
|  |  |  |  | 290 |  |  |  |  | 295 |  |  |  |  | 300 |  |

| TAT | GAT | ATG | AGG | AAA | TTG | CTG | AAC | GGT | ACG | GTC | GTT | TCC | AAG | CAT | CCG | 1419
| Tyr | Asp | Met | Arg | Lys | Leu | Leu | Asn | Gly | Thr | Val | Val | Ser | Lys | His | Pro |
|  |  |  | 305 |  |  |  |  | 310 |  |  |  |  | 315 |  |  |

| TTG | AAA | TCG | GTT | ACA | TTT | GTC | GAT | AAC | CAT | GAT | ACA | CAG | CCG | GGG | CAA | 1467
| Leu | Lys | Ser | Val | Thr | Phe | Val | Asp | Asn | His | Asp | Thr | Gln | Pro | Gly | Gln |
|  |  | 320 |  |  |  |  | 325 |  |  |  |  | 330 |  |  |  |

| TCG | CTT | GAG | TCG | ACT | GTC | CAA | ACA | TGG | TTT | AAG | CCG | CTT | GCT | TAC | GCT | 1515
| Ser | Leu | Glu | Ser | Thr | Val | Gln | Thr | Trp | Phe | Lys | Pro | Leu | Ala | Tyr | Ala |
|  | 335 |  |  |  |  | 340 |  |  |  |  | 345 |  |  |  |  |

| TTT | ATT | CTC | ACA | AGG | GAA | TCT | GGA | TAC | CCT | CAG | GTT | TTC | TAC | GGG | GAT | 1563
| Phe | Ile | Leu | Thr | Arg | Glu | Ser | Gly | Tyr | Pro | Gln | Val | Phe | Tyr | Gly | Asp |
| 350 |  |  |  |  | 355 |  |  |  |  | 360 |  |  |  |  | 365 |

| ATG | TAC | GGG | ACG | AAA | GGA | GAC | TCC | CAG | CGC | GAA | ATT | CCT | GCC | TTG | AAA | 1611
| Met | Tyr | Gly | Thr | Lys | Gly | Asp | Ser | Gln | Arg | Glu | Ile | Pro | Ala | Leu | Lys |
|  |  |  |  | 370 |  |  |  |  | 375 |  |  |  |  | 380 |  |

| CAC | AAA | ATT | GAA | CCG | ATC | TTA | AAA | GCG | AGA | AAA | CAG | TAT | GCG | TAC | GGA | 1659
| His | Lys | Ile | Glu | Pro | Ile | Leu | Lys | Ala | Arg | Lys | Gln | Tyr | Ala | Tyr | Gly |
|  |  |  | 385 |  |  |  |  | 390 |  |  |  |  | 395 |  |  |

| GCA | CAG | CAT | GAT | TAT | TTC | GAC | CAC | CAT | GAC | ATT | GTC | GGC | TGG | ACA | AGG | 1707
| Ala | Gln | His | Asp | Tyr | Phe | Asp | His | His | Asp | Ile | Val | Gly | Trp | Thr | Arg |
|  |  | 400 |  |  |  |  | 405 |  |  |  |  | 410 |  |  |  |

| GAA | GGC | GAC | AGC | TCG | GTT | GCA | AAT | TCA | GGT | TTG | GCG | GCA | TTA | ATA | ACA | 1755
| Glu | Gly | Asp | Ser | Ser | Val | Ala | Asn | Ser | Gly | Leu | Ala | Ala | Leu | Ile | Thr |
|  | 415 |  |  |  |  | 420 |  |  |  |  | 425 |  |  |  |  |

```
GAC GGA CCC GGT GGG GCA AAG CGA ATG TAT GTC GGC CGG CAA AAC GCC   1803
Asp Gly Pro Gly Gly Ala Lys Arg Met Tyr Val Gly Arg Gln Asn Ala
430                 435                 440                 445

GGT GAG ACA TGG CAT GAC ATT ACC GGA AAC CGT TCG GAG CCG GTT GTC   1851
Gly Glu Thr Trp His Asp Ile Thr Gly Asn Arg Ser Glu Pro Val Val
                450                 455                 460

ATC AAT TCG GAA GGC TGG GGA GAG TTT CAC GTA AAC GGC GGG TCG GTT   1899
Ile Asn Ser Glu Gly Trp Gly Glu Phe His Val Asn Gly Gly Ser Val
            465                 470                 475

TCA ATT TAT GTT CAA AGA TAGAAGAGCA GAGAGGACGG ATTTCCTGAA           1947
Ser Ile Tyr Val Gln Arg
        480

GGAAATCCGT TTTTTATTT TGCCCGTCTT ATAAATTTCT TTGATTACAT TTTATAATTA   2007

ATTTTAACAA AGTGTCATCA GCCCTCAGGA AGGACTTGCT GACAGTTTGA ATCGCATAGG  2067

TAAGGCGGGG ATGAAATGGC AACGTTATCT GATGTAGCAA AGAAAGCAAA TGTGTCGAAA  2127

ATGACGGTAT CGCGGGTGAT CA                                           2149
```

( 2 ) INFORMATION FOR SEQ ID NO:3:

( i ) SEQUENCE CHARACTERISTICS:
        ( A ) LENGTH: 512 amino acids
        ( B ) TYPE: amino acid
        ( D ) TOPOLOGY: linear ( x i ) SEQUENCE DESCRIPTION: SEQ ID NO:3:

```
Met Lys Gln Gln Lys Arg Leu Tyr Ala Arg Ser Val Thr Leu Leu Phe
-29             -25                 -20                 -15

Ala Leu Ile Phe Leu Leu Pro His Ser Ala Ala Ala Ala Ala Asn Leu
            -10                 -5                   1

Asn Gly Thr Leu Met Gln Tyr Phe Glu Trp Tyr Met Pro Asn Asp Gly
      5                 10                 15

Gln His Trp Lys Arg Leu Gln Asn Asp Ser Ala Tyr Leu Ala Glu His
    20              25                 30                      35

Gly Ile Thr Ala Val Trp Ile Pro Pro Ala Tyr Lys Gly Thr Ser Gln
                40                  45                 50

Ala Asp Val Gly Tyr Gly Ala Tyr Asp Leu Tyr Asp Leu Gly Glu Phe
            55                  60                  65

His Gln Lys Gly Thr Val Arg Thr Lys Tyr Gly Thr Lys Gly Glu Leu
        70                  75                  80

Gln Ser Ala Ile Lys Ser Leu His Ser Arg Asp Ile Asn Val Tyr Gly
    85                  90                  95

Asp Val Val Ile Asn His Lys Gly Gly Ala Asp Ala Thr Glu Asp Val
100                 105                 110                 115

Thr Ala Val Glu Val Asp Pro Ala Asp Arg Asn Arg Val Ile Ser Gly
                120                 125                 130

Glu His Leu Ile Lys Ala Trp Thr His Phe His Phe Pro Gly Arg Gly
            135                 140                 145

Ser Thr Tyr Ser Asp Phe Lys Trp His Trp Tyr His Phe Asp Gly Thr
        150                 155                 160

Asp Trp Asp Glu Ser Arg Lys Leu Asn Arg Ile Tyr Lys Phe Gln Gly
    165                 170                 175

Lys Ala Trp Asp Trp Glu Val Ser Asn Glu Asn Gly Asn Tyr Asp Tyr
180                 185                 190                 195

Leu Met Tyr Ala Asp Ile Asp Tyr Asp His Pro Asp Val Ala Ala Glu
                200                 205                 210

Ile Lys Arg Trp Gly Thr Trp Tyr Ala Asn Glu Leu Gln Leu Asp Gly
            215                 220                 225
```

| | | | | | | | | | | | | | |
|---|---|---|---|---|---|---|---|---|---|---|---|---|---|
| Phe | Arg | Leu | Asp | Ala | Val | Lys | His | Ile | Lys | Phe | Ser | Phe | Leu | Arg | Asp |
| | | 230 | | | | | 235 | | | | 240 | | | | |
| Trp | Val | Asn | His | Val | Arg | Glu | Lys | Thr | Gly | Lys | Glu | Met | Phe | Thr | Val |
| | 245 | | | | | 250 | | | | | 255 | | | | |
| Ala | Glu | Tyr | Trp | Gln | Asn | Asp | Leu | Gly | Ala | Leu | Glu | Asn | Tyr | Leu | Asn |
| 260 | | | | | 265 | | | | | 270 | | | | | 275 |
| Lys | Thr | Asn | Phe | Asn | His | Ser | Val | Phe | Asp | Val | Pro | Leu | His | Tyr | Gln |
| | | | | 280 | | | | | 285 | | | | | 290 | |
| Phe | His | Ala | Ala | Ser | Thr | Gln | Gly | Gly | Tyr | Asp | Met | Arg | Lys | Leu |
| | | | 295 | | | | | 300 | | | | 305 | | |
| Leu | Asn | Gly | Thr | Val | Val | Ser | Lys | His | Pro | Leu | Lys | Ser | Val | Thr | Phe |
| | | 310 | | | | | 315 | | | | | 320 | | | |
| Val | Asp | Asn | His | Asp | Thr | Gln | Pro | Gly | Gln | Ser | Leu | Glu | Ser | Thr | Val |
| | 325 | | | | | 330 | | | | | 335 | | | | |
| Gln | Thr | Trp | Phe | Lys | Pro | Leu | Ala | Tyr | Ala | Phe | Ile | Leu | Thr | Arg | Glu |
| 340 | | | | | 345 | | | | | 350 | | | | | 355 |
| Ser | Gly | Tyr | Pro | Gln | Val | Phe | Tyr | Gly | Asp | Met | Tyr | Gly | Thr | Lys | Gly |
| | | | | 360 | | | | | 365 | | | | | 370 | |
| Asp | Ser | Gln | Arg | Glu | Ile | Pro | Ala | Leu | Lys | His | Lys | Ile | Glu | Pro | Ile |
| | | | 375 | | | | | 380 | | | | | 385 | | |
| Leu | Lys | Ala | Arg | Lys | Gln | Tyr | Ala | Tyr | Gly | Ala | Gln | His | Asp | Tyr | Phe |
| | | 390 | | | | | 395 | | | | | 400 | | | |
| Asp | His | His | Asp | Ile | Val | Gly | Trp | Thr | Arg | Glu | Gly | Asp | Ser | Ser | Val |
| | 405 | | | | | 410 | | | | | 415 | | | | |
| Ala | Asn | Ser | Gly | Leu | Ala | Ala | Leu | Ile | Thr | Asp | Gly | Pro | Gly | Gly | Ala |
| 420 | | | | | 425 | | | | | 430 | | | | | 435 |
| Lys | Arg | Met | Tyr | Val | Gly | Arg | Gln | Asn | Ala | Gly | Glu | Thr | Trp | His | Asp |
| | | | | 440 | | | | | 445 | | | | | 450 | |
| Ile | Thr | Gly | Asn | Arg | Ser | Glu | Pro | Val | Val | Ile | Asn | Ser | Glu | Gly | Trp |
| | | | 455 | | | | | 460 | | | | | 465 | | |
| Gly | Glu | Phe | His | Val | Asn | Gly | Gly | Ser | Val | Ser | Ile | Tyr | Val | Gln | Arg |
| | | | 470 | | | | 475 | | | | | 480 | | | |

( 2 ) INFORMATION FOR SEQ ID NO:4:

( i ) SEQUENCE CHARACTERISTICS:
        ( A ) LENGTH: 5677 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 3882..5420

( i x ) FEATURE:
        ( A ) NAME/KEY: matpeptide
        ( B ) LOCATION: 3969..5420

( x i ) SEQUENCE DESCRIPTION: SEQ ID NO:4:

```
AATTCACCTC GAAAGCAAGC TGATAAACCG ATACAATTAA AGGCTCCTTT TGGAGCCTTT      60

TTTTTGGAG  ATTTTCAACG TGAAAAAATT ATTATTCGCA ATTCCAAGCT AATTCACCTC     120

GAAAGCAAGC TGATAAACCG ATACAATTAA AGGCTCCTTT TGGAGCCTTT TTTTTGGAG     180

ATTTTCAACG TGAAAAAATT ATTATTCGCA ATTCCAAGCT CTGCCTCGCG CGTTTCGGTG     240

ATGACGGTGA AAACCTCTGA CACATGCAGC TCCCGGAGAC GGTCACAGCT TGTCTGTAAG     300

CGGATGCAGA TCACGCGCCC TGTAGCGGCG CATTAAGCGC GGCGGGTGTG GTGGTTACGC     360

GCAGCGTGAC CGCTACACTT GCCAGCGCCC TAGCGCCCGC TCCTTTCGCT TTCTTCCCTT     420

CCTTTCTCGC CACGTTCGCC GGCTTTCCCC GTCAAGCTCT AAATCGGGGG CTCCCTTTAG     480
```

```
GGTTCCGATT TAGTGCTTTA CGGCACCTCG ACCCCAAAAA ACTTGATTAG GGTGATGGTT  540
CACGTAGTGG GCCATCGCCC TGATAGACGG TTTTTCGCCC TTTGACGTTG GAGTCCACGT  600
TCTTTAATAG TGGACTCTTG TTCCAAACTG GAACAACACT CAACCCTATC TCGGTCTATT  660
CTTTTGATTT ATAAGGGATT TTGCCGATTT CGGCCTATTG GTTAAAAAAT GAGCTGATTT  720
AACAAAAATT TAACGCGAAT TTTAACAAAA TATTAACGTT TACAATTTGA TCTGCGCTCG  780
GTCGTTCGGC TGCGGCGAGC GGTATCAGCT CACTCAAAGG CGGTAATACG GTTATCCACA  840
GAATCAGGGG ATAACGCAGG AAAGAACATG TGAGCAAAAG GCCAGCAAAA GGCCAGGAAC  900
CGTAAAAAGG CCGCGTTGCT GGCGTTTTTC CATAGGCTCC GCCCCCCTGA CGAGCATCAC  960
AAAAATCGAC GCTCAAGTCA GAGGTGGCGA AACCCGACAG GACTATAAAG ATACCAGGCG 1020
TTTCCCCCTG GAAGCTCCCT CGTGCGCTCT CCTGTTCCGA CCCTGCCGCT TACCGGATAC 1080
CTGTCCGCCT TTCTCCCTTC GGGAAGCGTG GCGCTTTCTC AATGCTCACG CTGTAGGTAT 1140
CTCAGTTCGG TGTAGGTCGT TCGCTCCAAG CTGGGCTGTG TGCACGAACC CCCCGTTCAG 1200
CCCGACCGCT GCGCCTTATC CGGTAACTAT CGTCTTGAGT CCAACCCGGT AAGACACGAC 1260
TTATCGCCAC TGGCAGCAGC CACTGGTAAC AGGATTAGCA GAGCGAGGTA TGTAGGCGGT 1320
GCTACAGAGT TCTTGAAGTG GTGGCCTAAC TACGGCTACA CTAGAAGGAC AGTATTTGGT 1380
ATCTGCGCTC TGCTGAAGCC AGTTACCTTC GGAAAAAGAG TTGGTAGCTC TTGATCCGGC 1440
AAACAAACCA CCGCTGGTAG CGGTGGTTTT TTTGTTTGCA AGCAGCAGAT TACGCGCAGA 1500
AAAAAAGGAT CTCAAGAAGA TCCTTTGATC TTTTCTACGG GGTCTGACGC TCAGTGGAAC 1560
GAAAACTCAC GTTAAGGGAT TTTGGTCATG AGATTATCAA AAAGGATCTT CACCTAGATC 1620
CTTTTAAATT AAAAATGAAG TTTTAAATCA ATCTAAAGTA TATATGAGTA AACTTGGTCT 1680
GACAGTTACC AATGCTTAAT CAGTGAGGCA CCTATCTCAG CGATCTGTCT ATTTCGTTCA 1740
TCCATAGTTG CCTGACTCCC CGTCGTGTAG ATAACTACGA TACGGGAGGG CTTACCATCT 1800
GGCCCCAGTG CTGCAATGAT ACCGCGAGAC CCACGCTCAC CGGCTCCAGA TTTATCAGCA 1860
ATAAACCAGC CAGCCGGAAG GGCCGAGCGC AGAAGTGGTC CTGCAACTTT ATCCGCCTCC 1920
ATCCAGTCTA TTAATTGTTG CCGGGAAGCT AGAGTAAGTA GTTCGCCAGT TAATAGTTTG 1980
CGCAACGTTG TTGCCATTGC TGCAGGCATC GTGGTGTCAC GCTCGTCGTT TGGTATGGCT 2040
TCATTCAGCT CCGGTTCCCA ACGATCAAGG CGAGTTACAT GATCCCCCAT GTTGTGCAAA 2100
AAAGCGGTTA GCTCCTTCGG TCCTCCGATC GTTGTCAGAA GTAAGTTGGC CGCAGTGTTA 2160
TCACTCATGG TTATGGCAGC ACTGCATAAT TCTCTTACTG TCATGCCATC CGTAAGATGC 2220
TTTTCTGTGA CTGGTGAGTA CTCAACCAAG TCATTCTGAG AATAGTGTAT GCGGCGACCG 2280
AGTTGCTCTT GCCCGGCGTC AACACGGGAT AATACCGCGC CACATAGCAG AACTTTAAAA 2340
GTGCTCATCA TTGGAAAACG TTCTTCGGGG CGAAAACTCT CAAGGATCTT ACCGCTGTTG 2400
AGATCCAGTT CGATGTAACC CACTCGTGCA CCCAACTGAT CTTCAGCATC TTTTACTTTC 2460
ACCAGCGTTT CTGGGTGAGC AAAAACAGGA AGGCAAAATG CCGCAAAAAA GGGAATAAGG 2520
GCGACACGGA AATGTTGAAT ACTCATACTC TTCCTTTTTC AATATTATTG AAGCAGACAG 2580
TTTTATTGTT CATGATGATA TATTTTTATC TTGTGCAATG TAACATCAGA GATTTTGAGA 2640
CACAACGTGG CTTTGTTGAA TAAATCGAAC TTTTGCTGAG TTGACTCCCC GCGCGCGATG 2700
GGTCGAATTT GCTTTCGAAA AAAAGCCCG CTCATTAGGC GGGCTAAAAA AAGCCCGCT 2760
CATTAGGCGG GCTCGAATTT CTGCCATTCA TCCGCTTATT ATCACTTATT CAGGCGTAGC 2820
AACCAGGCGT TTAAGGGCAC CAATAACTGC CTTAAAAAAA TTACGCCCCG CCCTGCCACT 2880
CATCGCAGTA CTGTTGTAAT TCATTAAGCA TTCTGCCGAC ATGGAAGCCA TCACAGACGG 2940
```

-continued

```
CATGATGAAC CTGAATCGCC AGCGGCATCA GCACCTTGTC GCCTTGCGTA TAATATTTGC 3000
CCATAGTGAA AACGGGGGCG AAGAAGTTGT CCATATTCGC CACGTTTAAA TCAAAACTGG 3060
TGAAACTCAC CCAGGGATTG GCTGAGACGA AAACATATT CTCAATAAAC CCTTTAGGGA 3120
AATAGGCCAG GTTTTCACCG TAACACGCCA CATCTTGCGA ATATATGTGT AGAAACTGCC 3180
GGAAATCGTC GTGGTATTCA CTCCAGAGCG ATGAAAACGT TTCAGTTTGC TCATGGAAAA 3240
CGGTGTAACA AGGGTGAACA CTATCCCATA TCACCAGCTC ACCGTCTTTC ATTGCCATAC 3300
GAAATTCCGG ATGAGCATTC ATCAGGCGGG CAAGAATGTG AATAAAGGCC GGATAAAACT 3360
TGTGCTTATT TTTCTTTACG GTCTTTAAAA AGGCCGTAAT ATCCAGCTAA ACGGTCTGGT 3420
TATAGGTACA TTGAGCAACT GACTGAAATG CCTCAAAATG TTCTTTACGA TGCCATTGGG 3480
ATATATCAAC GGTGGTATAT CCAGTGATTT TTTTCTCCAT TTTAGCTTCC TTAGCTCCTG 3540
AAAATCTCGA TAACTCAAAA AATACGCCCG GTAGTGATCT TATTTCATTA TGGTGAAAGT 3600
TGGAACCTCT TACGTGCCGA TCAACGTCTC ATTTCGCCA AAAGTTGGCC CAGGGCTTCC 3660
CGGTATCAAC AGGGACACCA GGATTTATTT ATTCTGCGAA GTGATCTTCC GTCACAGGTA 3720
TTTATTCGAA GACGAAGGG CATCGCGCGC GGGGAATTCG AGCTCGAGCT TACTCCCCAT 3780
CCCCCTGTTG ACAATTAATC ATCGGCTCGT ATAATGTGTG GAATTGTGAG CGGATAACAA 3840
TTTCACACAG GAAACAGGAT CCAAGGAGGT GATCTAGAGT C ATG AAA CAA CAA       3893
                                              Met Lys Gln Gln
                                               -29

AAA CGG CTT TAC GCC CGA TTG CTG ACG CTG TTA TTT GCG CTC ATC TTC   3941
Lys Arg Leu Tyr Ala Arg Leu Leu Thr Leu Leu Phe Ala Leu Ile Phe
-25             -20              -15              -10

TTG CTG CCT CAT TCT GCA GCA GCG GCG GCA AAT CTT AAT GGG ACG CTG   3989
Leu Leu Pro His Ser Ala Ala Ala Ala Ala Asn Leu Asn Gly Thr Leu
            -5               1                5

ATG CAG TAT TTT GAA TGG TAC ATG CCC AAT GAC GGC CAA CAT TGG AAG   4037
Met Gln Tyr Phe Glu Trp Tyr Met Pro Asn Asp Gly Gln His Trp Lys
         10              15               20

CGT TTG CAA AAC GAC TCG GCA TAT TTG GCT GAA CAC GGT ATT ACT GCC   4085
Arg Leu Gln Asn Asp Ser Ala Tyr Leu Ala Glu His Gly Ile Thr Ala
     25              30               35

GTC TGG ATT CCC CCG GCA TAT AAG GGA ACT AGT CAA GCG GAT GTG GGC   4133
Val Trp Ile Pro Pro Ala Tyr Lys Gly Thr Ser Gln Ala Asp Val Gly
40               45               50                              55

TAC GGT GCT TAC GAC CTT TAT GAT TTA GGG GAG TTT CAT CAA AAA GGG   4181
Tyr Gly Ala Tyr Asp Leu Tyr Asp Leu Gly Glu Phe His Gln Lys Gly
             60               65               70

ACG GTT CGG ACA AAG TAC GGC ACA AAA GGA GAG CTG CAA TCT GCG ATC   4229
Thr Val Arg Thr Lys Tyr Gly Thr Lys Gly Glu Leu Gln Ser Ala Ile
         75              80               85

AAA AGT CTT CAT TCC CGC GAC ATT AAC GTT TAC GGG GAT GTG GTC ATC   4277
Lys Ser Leu His Ser Arg Asp Ile Asn Val Tyr Gly Asp Val Val Ile
     90              95               100

AAC CAC AAA GGC GGC GCT GAT GCG ACC GAA GAT GTA ACC GCG GTT GAA   4325
Asn His Lys Gly Gly Ala Asp Ala Thr Glu Asp Val Thr Ala Val Glu
105              110              115

GTC GAT CCC GCT GAC CGC AAC CGC GTA ATT TCA GGA GAA CAC CTA ATT   4373
Val Asp Pro Ala Asp Arg Asn Arg Val Ile Ser Gly Glu His Leu Ile
120          125              130                          135

AAA GCC TGG ACA CAT TTT CAT TTT CCG GGG CGC GGC AGC ACA TAC AGC   4421
Lys Ala Trp Thr His Phe His Phe Pro Gly Arg Gly Ser Thr Tyr Ser
             140              145              150

GAT TTT AAA TGG CAT TGG TAC CAT TTT GAC GGA ACC GAT TGG GAC GAG   4469
Asp Phe Lys Trp His Trp Tyr His Phe Asp Gly Thr Asp Trp Asp Glu
```

|  |  |  |  |  |  |  |  |  |  |  |  |  |  |  |  |  |
|---|---|---|---|---|---|---|---|---|---|---|---|---|---|---|---|---|
|  |  |  | 155 |  |  |  |  | 160 |  |  |  |  |  | 165 |  |  |
| TCC | CGA | AAG | CTG | AAC | CGC | ATC | TAT | AAG | TTT | CAA | GGA | AAG | GCT | TGG | GAT | 4517 |
| Ser | Arg | Lys 170 | Leu | Asn | Arg | Ile | Tyr 175 | Lys | Phe | Gln | Gly | Lys 180 | Ala | Trp | Asp |  |
| TGG | GAA | GTT | TCC | AAT | GAA | AAC | GGC | AAC | TAT | GAT | TAT | TTG | ATG | TAT | GCC | 4565 |
| Trp | Glu 185 | Val | Ser | Asn | Glu | Asn 190 | Gly | Asn | Tyr | Asp | Tyr 195 | Leu | Met | Tyr | Ala |  |
| GAC | ATC | GAT | TAT | GAC | CAT | CCT | GAT | GTC | GCA | GCA | GAA | ATT | AAG | AGA | TGG | 4613 |
| Asp 200 | Ile | Asp | Tyr | Asp | His 205 | Pro | Asp | Val | Ala | Ala 210 | Glu | Ile | Lys | Arg | Trp 215 |  |
| GGC | ACT | TGG | TAT | GCC | AAT | GAA | CTG | CAA | TTG | GAC | GGT | TTC | CGT | CTT | GAT | 4661 |
| Gly | Thr | Trp | Tyr | Ala 220 | Asn | Glu | Leu | Gln | Leu 225 | Asp | Gly | Phe | Arg | Leu 230 | Asp |  |
| GCT | GTC | AAA | CAC | ATT | AAA | TTT | TCT | TTT | TTG | CGG | GAT | TGG | GTT | AAT | CAT | 4709 |
| Ala | Val | Lys | His 235 | Ile | Lys | Phe | Ser | Phe 240 | Leu | Arg | Asp | Trp | Val 245 | Asn | His |  |
| GTC | AGG | GAA | AAA | ACG | GGG | AAG | GAA | ATG | TTT | ACG | GTA | GCT | GAA | TAT | TGG | 4757 |
| Val | Arg | Glu 250 | Lys | Thr | Gly | Lys | Glu 255 | Met | Phe | Thr | Val | Ala 260 | Glu | Tyr | Trp |  |
| CAG | AAT | GAC | TTG | GGC | GCC | CTG | GAA | AAC | TAT | TTG | AAC | AAA | ACA | AAT | TTT | 4805 |
| Gln | Asn | Asp 265 | Leu | Gly | Ala | Leu | Glu 270 | Asn | Tyr | Leu | Asn | Lys 275 | Thr | Asn | Phe |  |
| AAT | CAT | TCA | GTG | TTT | GAC | GTG | CCG | CTT | CAT | TAT | CAG | TTC | CAT | GCT | GCA | 4853 |
| Asn 280 | His | Ser | Val | Phe | Asp 285 | Val | Pro | Leu | His | Tyr 290 | Gln | Phe | His | Ala | Ala 295 |  |
| TCG | ACA | CAG | GGA | GGC | GGC | TAT | GAT | ATG | AGG | AAA | TTG | CTG | AAC | GGT | ACG | 4901 |
| Ser | Thr | Gln | Gly | Gly 300 | Gly | Tyr | Asp | Met | Arg 305 | Lys | Leu | Leu | Asn | Gly 310 | Thr |  |
| GTC | GTT | TCC | AAG | CAT | CCG | TTG | AAA | TCG | GTT | ACA | TTT | GTC | GAT | AAC | CAT | 4949 |
| Val | Val | Ser | Lys 315 | His | Pro | Leu | Lys | Ser 320 | Val | Thr | Phe | Val | Asp 325 | Asn | His |  |
| GAT | ACA | CAG | CCG | GGG | CAA | TCG | CTT | GAG | TCG | ACT | GTC | CAA | ACA | TGG | TTT | 4997 |
| Asp | Thr | Gln | Pro 330 | Gly | Gln | Ser | Leu | Glu 335 | Ser | Thr | Val | Gln | Thr 340 | Trp | Phe |  |
| AAG | CCG | CTT | GCT | TAC | GCT | TTT | ATT | CTC | ACA | AGG | GAA | TCT | GGA | TAC | CCT | 5045 |
| Lys | Pro 345 | Leu | Ala | Tyr | Ala | Phe 350 | Ile | Leu | Thr | Arg | Glu 355 | Ser | Gly | Tyr | Pro |  |
| CAG | GTT | TTC | TAC | GGG | GAT | ATG | TAC | GGG | ACG | AAA | GGA | GAC | TCC | CAG | CGC | 5093 |
| Gln 360 | Val | Phe | Tyr | Gly | Asp 365 | Met | Tyr | Gly | Thr | Lys 370 | Gly | Asp | Ser | Gln | Arg 375 |  |
| GAA | ATT | CCT | GCC | TTG | AAA | CAC | AAA | ATT | GAA | CCG | ATC | TTA | AAA | GCG | AGA | 5141 |
| Glu | Ile | Pro | Ala | Leu 380 | Lys | His | Lys | Ile | Glu 385 | Pro | Ile | Leu | Lys | Ala 390 | Arg |  |
| AAA | CAG | TAT | GCG | TAC | GGA | GCA | CAG | CAT | GAT | TAT | TTC | GAC | CAC | CAT | GAC | 5189 |
| Lys | Gln | Tyr | Ala 395 | Tyr | Gly | Ala | Gln | His 400 | Asp | Tyr | Phe | Asp | His 405 | His | Asp |  |
| ATT | GTC | GGC | TGG | ACA | AGG | GAA | GGC | GAC | AGC | TCG | GTT | GCA | AAT | TCA | GGT | 5237 |
| Ile | Val | Gly | Trp 410 | Thr | Arg | Glu | Gly | Asp 415 | Ser | Ser | Val | Ala | Asn 420 | Ser | Gly |  |
| TTG | GCG | GCA | TTA | ATA | ACA | GAC | GGA | CCC | GGT | GGG | GCA | AAG | CGA | ATG | TAT | 5285 |
| Leu | Ala | Ala | Leu 425 | Ile | Thr | Asp | Gly | Pro 430 | Gly | Gly | Ala | Lys | Arg 435 | Met | Tyr |  |
| GTC | GGC | CGG | CAA | AAC | GCC | GGT | GAG | ACA | TGG | CAT | GAC | ATT | ACC | GGA | AAC | 5333 |
| Val | Gly 440 | Arg | Gln | Asn | Ala | Gly 445 | Glu | Thr | Trp | His | Asp 450 | Ile | Thr | Gly | Asn 455 |  |
| CGT | TCG | GAG | CCG | GTT | GTC | ATC | AAT | TCG | GAA | GGC | TGG | GGA | GAG | TTT | CAC | 5381 |
| Arg | Ser | Glu | Pro | Val 460 | Val | Ile | Asn | Ser | Glu 465 | Gly | Trp | Gly | Glu | Phe 470 | His |  |
| GTA | AAC | GGC | GGG | TCG | GTT | TCA | ATT | TAT | GTT | CAA | AGA | TAGGTGACCA |  |  |  | 5427 |
| Val | Asn | Gly | Gly 475 | Ser | Val | Ser | Ile | Tyr 480 | Val | Gln | Arg |  |  |  |  |  |

```
GAGAGGACGG ATTTCCTGAA GGAAATCCGT TTTTTTATTT TGCCCGTCTT ATAAATTTCT    5487

TTGATTACAT TTTATAATTA ATTTTAACAA AGTGTCATCA GCCCTCAGGA AGGACTTGCT    5547

GACAGTTTGA ATCGCATAGG TAAGGCGGGG ATGAAATGGC AACGTTATCT GATGTAGCAA    5607

AGAAAGCAAA TGTGTCGAAA ATGACGGTAT CGCGGGTGAT CCTCTAGAAG AAGCTTGGTC    5667

TAGAGGTCGA                                                          5677
```

( 2 ) INFORMATION FOR SEQ ID NO:5:

( i ) SEQUENCE CHARACTERISTICS:
        ( A ) LENGTH: 512 amino acids
        ( B ) TYPE: amino acid
        ( D ) TOPOLOGY: linear ( x i ) SEQUENCE DESCRIPTION: SEQ ID NO:5:

```
Met  Lys  Gln  Gln  Lys  Arg  Leu  Tyr  Ala  Arg  Leu  Leu  Thr  Leu  Leu  Phe
-29            -25                      -20                      -15

Ala  Leu  Ile  Phe  Leu  Leu  Pro  His  Ser  Ala  Ala  Ala  Ala  Ala  Asn  Leu
               -10                       -5                       1

Asn  Gly  Thr  Leu  Met  Gln  Tyr  Phe  Glu  Trp  Tyr  Met  Pro  Asn  Asp  Gly
      5                      10                      15

Gln  His  Trp  Lys  Arg  Leu  Gln  Asn  Asp  Ser  Ala  Tyr  Leu  Ala  Glu  His
 20                 25                      30                            35

Gly  Ile  Thr  Ala  Val  Trp  Ile  Pro  Pro  Ala  Tyr  Lys  Gly  Thr  Ser  Gln
                40                      45                           50

Ala  Asp  Val  Gly  Tyr  Gly  Ala  Tyr  Asp  Leu  Tyr  Asp  Leu  Gly  Glu  Phe
           55                      60                      65

His  Gln  Lys  Gly  Thr  Val  Arg  Thr  Lys  Tyr  Gly  Thr  Lys  Gly  Glu  Leu
               70                      75                      80

Gln  Ser  Ala  Ile  Lys  Ser  Leu  His  Ser  Arg  Asp  Ile  Asn  Val  Tyr  Gly
      85                      90                      95

Asp  Val  Val  Ile  Asn  His  Lys  Gly  Gly  Ala  Asp  Ala  Thr  Glu  Asp  Val
100                      105                      110                      115

Thr  Ala  Val  Glu  Val  Asp  Pro  Ala  Asp  Arg  Asn  Arg  Val  Ile  Ser  Gly
                120                      125                      130

Glu  His  Leu  Ile  Lys  Ala  Trp  Thr  His  Phe  His  Phe  Pro  Gly  Arg  Gly
           135                      140                      145

Ser  Thr  Tyr  Ser  Asp  Phe  Lys  Trp  His  Trp  Tyr  His  Phe  Asp  Gly  Thr
          150                      155                      160

Asp  Trp  Asp  Glu  Ser  Arg  Lys  Leu  Asn  Arg  Ile  Tyr  Lys  Phe  Gln  Gly
165                      170                      175

Lys  Ala  Trp  Asp  Trp  Glu  Val  Ser  Asn  Glu  Asn  Gly  Asn  Tyr  Asp  Tyr
180                      185                      190                      195

Leu  Met  Tyr  Ala  Asp  Ile  Asp  Tyr  Asp  His  Pro  Asp  Val  Ala  Ala  Glu
               200                      205                      210

Ile  Lys  Arg  Trp  Gly  Thr  Trp  Tyr  Ala  Asn  Glu  Leu  Gln  Leu  Asp  Gly
                215                      220                      225

Phe  Arg  Leu  Asp  Ala  Val  Lys  His  Ile  Lys  Phe  Ser  Phe  Leu  Arg  Asp
           230                      235                      240

Trp  Val  Asn  His  Val  Arg  Glu  Lys  Thr  Gly  Lys  Glu  Met  Phe  Thr  Val
245                      250                      255

Ala  Glu  Tyr  Trp  Gln  Asn  Asp  Leu  Gly  Ala  Leu  Glu  Asn  Tyr  Leu  Asn
260                      265                      270                      275

Lys  Thr  Asn  Phe  Asn  His  Ser  Val  Phe  Asp  Val  Pro  Leu  His  Tyr  Gln
               280                      285                      290

Phe  His  Ala  Ala  Ser  Thr  Gln  Gly  Gly  Gly  Tyr  Asp  Met  Arg  Lys  Leu
               295                      300                      305
```

| | | | | | | | | | | | | | |
|---|---|---|---|---|---|---|---|---|---|---|---|---|---|
| Leu | Asn | Gly<br>310 | Thr | Val | Val | Ser<br>315 | Lys | His | Pro | Leu | Lys<br>320 | Ser | Val | Thr | Phe |
| Val<br>325 | Asp | Asn | His | Asp | Thr<br>330 | Gln | Pro | Gly | Gln | Ser<br>335 | Leu | Glu | Ser | Thr | Val |
| Gln<br>340 | Thr | Trp | Phe | Lys | Pro<br>345 | Leu | Ala | Tyr | Ala | Phe<br>350 | Ile | Leu | Thr | Arg | Glu<br>355 |
| Ser | Gly | Tyr | Pro | Gln<br>360 | Val | Phe | Tyr | Gly | Asp<br>365 | Met | Tyr | Gly | Thr | Lys<br>370 | Gly |
| Asp | Ser | Gln | Arg<br>375 | Glu | Ile | Pro | Ala | Leu<br>380 | Lys | His | Lys | Ile | Glu<br>385 | Pro | Ile |
| Leu | Lys | Ala | Arg<br>390 | Lys | Gln | Tyr | Ala<br>395 | Tyr | Gly | Ala | Gln | His<br>400 | Asp | Tyr | Phe |
| Asp | His<br>405 | His | Asp | Ile | Val | Gly<br>410 | Trp | Thr | Arg | Glu | Gly<br>415 | Asp | Ser | Ser | Val |
| Ala<br>420 | Asn | Ser | Gly | Leu | Ala<br>425 | Ala | Leu | Ile | Thr | Asp<br>430 | Gly | Pro | Gly | Gly | Ala<br>435 |
| Lys | Arg | Met | Tyr | Val<br>440 | Gly | Arg | Gln | Asn | Ala<br>445 | Gly | Glu | Thr | Trp | His<br>450 | Asp |
| Ile | Thr | Gly | Asn<br>455 | Arg | Ser | Glu | Pro | Val<br>460 | Val | Ile | Asn | Ser | Glu<br>465 | Gly | Trp |
| Gly | Glu | Phe<br>470 | His | Val | Asn | Gly | Gly<br>475 | Ser | Val | Ser | Ile | Tyr<br>480 | Val | Gln | Arg |

(2) INFORMATION FOR SEQ ID NO:6:

(i) SEQUENCE CHARACTERISTICS:
      (A) LENGTH: 200 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 132..200

(xi) SEQUENCE DESCRIPTION: SEQ ID NO:6:

```
GAATTCGAGC TCGAGCTTAC TCCCCATCCC CCTGTTGACA ATTAATCATC GGCTCGTATA        60

ATGTGTGGAA TTGTGAGCGG ATAACAATTT CACACAGGAA ACAGGATCCG CGGATCCGTG       120

GAGAAAATAA A GTG AAA CAA AGC ACT ATT GCA CTG GCA CTC TTA CCG TTA       170
            Met Lys Gln Ser Thr Ile Ala Leu Ala Leu Leu Pro Leu
             1               5                  10

CTG TTT ACC CCT GTG ACA AAA GCG GCA AAT                                 200
Leu Phe Thr Pro Val Thr Lys Ala Ala Asn
 15                  20
```

(2) INFORMATION FOR SEQ ID NO:7:

(i) SEQUENCE CHARACTERISTICS:
      (A) LENGTH: 23 amino acids
      (B) TYPE: amino acid
      (D) TOPOLOGY: linear (ii) MOLECULE TYPE: protein (xi) SEQUENCE DESCRIPTION: SEQ ID NO:7:

```
Met Lys Gln Ser Thr Ile Ala Leu Ala Leu Leu Pro Leu Leu Phe Thr
 1               5                  10                  15

Pro Val Thr Lys Ala Ala Asn
                20
```